(12) United States Patent
Bergheim et al.

(10) Patent No.: US 9,492,244 B2
(45) Date of Patent: Nov. 15, 2016

(54) LIQUID JET APPARATUS AND METHODS FOR DENTAL TREATMENTS

(75) Inventors: Bjarne Bergheim, Mission Viejo, CA (US); Morteza Gharib, San Marino, CA (US); Mehrzad Khakpour, Laguna Beach, CA (US); Michele Pham, Anaheim, CA (US); Richard S. Tebbs, Aliso Viejo, CA (US)

(73) Assignee: SONENDO, INC., Laguna Hills, CA (US)

( * ) Notice: Subject to any disclaimer, the term of this patent is extended or adjusted under 35 U.S.C. 154(b) by 132 days.

(21) Appl. No.: 12/945,791

(22) Filed: Nov. 12, 2010

(65) Prior Publication Data

US 2011/0117517 A1   May 19, 2011

Related U.S. Application Data

(60) Provisional application No. 61/261,293, filed on Nov. 13, 2009.

(51) Int. Cl.
  *A61C 17/02*   (2006.01)
  *A61C 5/02*   (2006.01)
  *A61C 17/028*   (2006.01)

(52) U.S. Cl.
  CPC ............... *A61C 5/02* (2013.01); *A61C 17/02* (2013.01); *A61C 17/028* (2013.01)

(58) Field of Classification Search
  CPC .......... A61C 5/02; A61C 17/02; A61C 17/028
  USPC .............................. 433/81, 88, 215, 216, 224
  See application file for complete search history.

(56) References Cited

U.S. PATENT DOCUMENTS

| 1,500,107 A | 7/1924 | Chandler |
| 3,023,306 A | 2/1962 | Kester |
| (Continued) | | |

FOREIGN PATENT DOCUMENTS

| AU | 2012-202315 | 4/2012 |
| AU | 2007140780 | 5/2014 |
| (Continued) | | |

OTHER PUBLICATIONS

European Extended Search Report, dated Sep. 22, 2011, for EP Application No. 07755777.5., in 7 pages.
(Continued)

*Primary Examiner* — Ralph Lewis
(74) *Attorney, Agent, or Firm* — Knobbe, Martens, Olson & Bear LLP

(57) ABSTRACT

Systems and methods for using a liquid jet apparatus for dental treatments are disclosed. In one implementation, the liquid jet apparatus may include a handpiece configured to deliver a high velocity liquid jet to a desired location in the mouth of a patient. The handpiece may include a positioning member having a channel through or along which the jet can propagate. The positioning member may have a distal end portion configured to be at least partially disposed in a pulp cavity, canal space, or opening in the tooth under treatment. During operation, the jet may impact an impingement surface of the distal end portion of the positioning member and be deflected as a spray through one or more openings in the distal end portion. The liquid jet apparatus may be used for root canal treatments.

79 Claims, 26 Drawing Sheets

(56) References Cited

U.S. PATENT DOCUMENTS

| | | |
|---|---|---|
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 10/1984 | Johnson, Jr. |
| 4,534,542 A | 8/1985 | Russo |
| 4,608,017 A | 8/1986 | Sadohara |
| 4,676,749 A | 6/1987 | Mabille |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,993,947 A * | 2/1991 | Grosrey ............... 433/81 |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,195,952 A | 3/1993 | Solnit et al. |
| 5,267,856 A | 12/1993 | Wolbarsht et al. |
| 5,295,828 A | 3/1994 | Grosrey |
| 5,307,839 A | 5/1994 | Loebker et al. |
| 5,322,504 A | 6/1994 | Doherty et al. |
| 5,380,201 A | 1/1995 | Kawata |
| 5,387,376 A | 2/1995 | Gasser |
| D356,866 S | 3/1995 | Meller |
| 5,435,724 A | 7/1995 | Goodman et al. |
| 5,474,451 A | 12/1995 | Dalrymple et al. |
| 5,490,779 A | 2/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,643,299 A | 7/1997 | Bair |
| 5,674,226 A | 10/1997 | Doherty et al. |
| 5,730,727 A | 3/1998 | Russo |
| 5,735,815 A | 4/1998 | Bair |
| 5,759,159 A | 6/1998 | Masreliez |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,839,896 A | 11/1998 | Hickok et al. |
| 5,842,863 A | 12/1998 | Bruns et al. |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,915,965 A | 6/1999 | Ohlsson et al. |
| 5,975,897 A | 11/1999 | Propp et al. |
| 5,989,023 A | 11/1999 | Summer et al. |
| 6,053,735 A | 4/2000 | Buchanan |
| 6,079,979 A | 6/2000 | Riitano |
| 6,122,300 A | 9/2000 | Freiberg et al. |
| 6,143,011 A | 11/2000 | Hood et al. |
| 6,159,006 A | 12/2000 | Cook et al. |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |
| 6,190,318 B1 | 2/2001 | Bab et al. |
| 6,221,031 B1 | 4/2001 | Heraud |
| 6,224,378 B1 * | 5/2001 | Valdes et al. ............... 433/224 |
| 6,227,855 B1 | 5/2001 | Hickok et al. |
| 6,245,032 B1 | 6/2001 | Sauer et al. |
| 6,290,502 B1 * | 9/2001 | Hugo ............... 433/215 |
| 6,312,440 B1 | 11/2001 | Hood et al. |
| 6,315,557 B1 | 11/2001 | Messick |
| 6,386,871 B1 | 5/2002 | Rossell |
| 6,390,815 B1 | 5/2002 | Pond |
| 6,440,103 B1 | 8/2002 | Hood et al. |
| 6,454,566 B1 | 9/2002 | Lynch et al. |
| 6,464,498 B1 | 10/2002 | Pond |
| 6,497,572 B2 | 12/2002 | Hood et al. |
| 6,511,493 B1 | 1/2003 | Moutafis et al. |
| 6,514,077 B1 | 2/2003 | Wilk |
| 6,527,766 B1 | 3/2003 | Bair |
| 6,562,050 B1 | 5/2003 | Owen |
| 6,572,709 B1 | 6/2003 | Kaneda et al. |
| 6,638,219 B1 | 10/2003 | Asch et al. |
| 6,641,394 B2 | 11/2003 | Garman |
| 6,817,862 B2 | 11/2004 | Hickok |
| D499,486 S | 12/2004 | Kuhn et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,644 B1 | 3/2006 | Andrew et al. |
| 7,044,737 B2 | 5/2006 | Fu |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,270,544 B2 | 9/2007 | Schemmer et al. |
| 7,306,577 B2 | 12/2007 | Lemoine et al. |
| 7,326,054 B2 | 2/2008 | Todd et al. |
| 7,549,861 B2 | 6/2009 | Ruddle et al. |
| 7,845,944 B2 | 12/2010 | DiGasbarro |
| 7,959,441 B2 | 6/2011 | Glover et al. |
| 7,980,854 B2 | 7/2011 | Glover et al. |
| 8,002,544 B2 | 8/2011 | Rizoiu et al. |
| 8,047,841 B2 | 11/2011 | Jefferies |
| 8,128,401 B2 | 3/2012 | Ruddle et al. |
| 8,204,612 B2 | 6/2012 | Feine et al. |
| D669,180 S | 10/2012 | Takashi et al. |
| 8,295,025 B2 | 10/2012 | Edel et al. |
| 8,317,514 B2 | 11/2012 | Weill |
| 8,322,910 B2 | 12/2012 | Gansmuller et al. |
| 8,506,293 B2 | 8/2013 | Pond |
| 8,617,090 B2 | 12/2013 | Fougere et al. |
| 8,684,956 B2 | 4/2014 | McDonough et al. |
| 8,747,005 B2 | 6/2014 | Kemp et al. |
| 8,753,121 B2 | 6/2014 | Gharib et al. |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,101,377 B2 | 8/2015 | Boutoussov et al. |
| D745,966 S | 12/2015 | Piorek et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 2002/0012897 A1 | 1/2002 | Tingley et al. |
| 2002/0072032 A1 | 6/2002 | Senn et al. |
| 2002/0108614 A1 | 8/2002 | Schultz |

(56) References Cited

U.S. PATENT DOCUMENTS

| | | |
|---|---|---|
| 2003/0096213 A1 | 5/2003 | Hickok et al. |
| 2003/0191429 A1 | 10/2003 | Andrew et al. |
| 2003/0207231 A1 | 11/2003 | Nance |
| 2003/0207232 A1 | 11/2003 | Todd et al. |
| 2004/0048226 A1 | 3/2004 | Garman |
| 2004/0063074 A1 | 4/2004 | Fisher |
| 2004/0072122 A1 | 4/2004 | Hegemann |
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1 | 8/2005 | Pond |
| 2005/0199261 A1 | 9/2005 | Vanhauwermeiren et al. |
| 2005/0271531 A1 | 12/2005 | Brown et al. |
| 2005/0277898 A1 | 12/2005 | Dimalanta et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0246395 A1 | 11/2006 | Pond |
| 2006/0257819 A1* | 11/2006 | Johnson .................... 433/86 |
| 2006/0264808 A1 | 11/2006 | Staid et al. |
| 2007/0009449 A1 | 1/2007 | Kanca |
| 2007/0020576 A1 | 1/2007 | Osborn et al. |
| 2007/0042316 A1 | 2/2007 | Pichat et al. |
| 2007/0083120 A1 | 4/2007 | Cain et al. |
| 2007/0148615 A1 | 6/2007 | Pond |
| 2007/0248932 A1* | 10/2007 | Gharib et al. ............. 433/81 |
| 2007/0287125 A1 | 12/2007 | Weill |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0155770 A1 | 7/2008 | Grez |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1 | 8/2008 | Teichert et al. |
| 2008/0255498 A1 | 10/2008 | Houle |
| 2008/0311540 A1 | 12/2008 | Gottenbos et al. |
| 2009/0004621 A1 | 1/2009 | Quan et al. |
| 2009/0011380 A1 | 1/2009 | Wang |
| 2009/0047624 A1 | 2/2009 | Tsai |
| 2009/0054881 A1 | 2/2009 | Krespi |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | DiVito et al. |
| 2009/0263759 A1 | 10/2009 | Van Herpern |
| 2010/0092922 A1 | 4/2010 | Ruddle |
| 2010/0143861 A1 | 6/2010 | Gharib et al. |
| 2010/0152634 A1 | 6/2010 | Dove |
| 2010/0160838 A1 | 6/2010 | Krespi |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0072605 A1 | 3/2011 | Steur |
| 2011/0087605 A1 | 4/2011 | Pond |
| 2011/0111365 A1 | 5/2011 | Gharib et al. |
| 2011/0143310 A1 | 6/2011 | Hunter |
| 2011/0229845 A1 | 9/2011 | Chen |
| 2011/0269099 A1 | 11/2011 | Glover et al. |
| 2011/0281231 A1 | 11/2011 | Rizoiu et al. |
| 2012/0135373 A1 | 5/2012 | Cheng et al. |
| 2012/0141953 A1 | 6/2012 | Mueller |
| 2012/0148979 A1 | 6/2012 | Ruddle |
| 2012/0237893 A1 | 9/2012 | Bergheim |
| 2012/0276497 A1 | 11/2012 | Gharib |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0143180 A1 | 6/2013 | Glover et al. |
| 2013/0177865 A1 | 7/2013 | Ostler |
| 2013/0216980 A1 | 8/2013 | Boronkay et al. |
| 2013/0236857 A1 | 9/2013 | Boutoussov et al. |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0080090 A1 | 3/2014 | Laufer |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1 | 5/2014 | Blaisdell et al. |
| 2014/0170588 A1 | 6/2014 | Miller et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147718 A1 | 5/2015 | Khakpour |
| 2015/0150650 A1 | 6/2015 | Netchitailo et al. |
| 2015/0173852 A1 | 6/2015 | Khakpour |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib |
| 2015/0374471 A1 | 12/2015 | Stangel et al. |
| 2016/0095679 A1 | 4/2016 | Khakpour |
| 2016/0100921 A1 | 4/2016 | Ungar |
| 2016/0113733 A1 | 4/2016 | Pond et al. |
| 2016/0135581 A1 | 5/2016 | Pai |

FOREIGN PATENT DOCUMENTS

| | | |
|---|---|---|
| AU | 2011316839 | 8/2015 |
| CA | 2361482 | 6/2002 |
| CN | 102724929 | 10/2012 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 2 498 713 | 9/2012 |
| EP | 2 934 364 | 10/2015 |
| EP | 2 951 019 | 12/2015 |
| EP | 3 013 277 | 5/2016 |
| FR | 1 225 547 | 7/1960 |
| FR | 2 831 050 | 10/2001 |
| GB | 917 633 | 2/1963 |
| HK | 1 188 108 A | 4/2014 |
| IL | 219169 | 4/2013 |
| IN | 8681/DELNP/2010 | 3/2012 |
| JP | 2000-254153 A | 9/2000 |
| JP | 2004-313659 | 11/2003 |
| JP | 2005-095374 | 4/2005 |
| JP | 2009-114953 | 5/2009 |
| JP | 2013-510688 | 3/2013 |

(56) References Cited

FOREIGN PATENT DOCUMENTS

| | | |
|---|---|---|
| JP | 2013-544120 | 12/2013 |
| JP | 2015-510829 | 4/2015 |
| JP | 2015-512761 | 4/2015 |
| JP | 5902096 | 3/2016 |
| KR | 10-2012-0084897 A | 7/2012 |
| WO | WO 92/12685 | 8/1992 |
| WO | WO 98/25536 | 6/1995 |
| WO | WO 00/45731 | 8/2000 |
| WO | WO 01/93773 | 12/2001 |
| WO | WO 02/078644 | 10/2002 |
| WO | WO 03/086223 | 10/2003 |
| WO | WO 2004/082501 | 9/2004 |
| WO | WO 2005/007008 A1 | 1/2005 |
| WO | WO 2005/032393 | 4/2005 |
| WO | WO 2006/082101 | 8/2006 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/064947 | 5/2009 |
| WO | WO 2009/137815 | 11/2009 |
| WO | WO 2010/099538 | 9/2010 |
| WO | WO 2011/060327 | 5/2011 |
| WO | WO 2012/054905 | 4/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2014/100751 | 6/2014 |
| WO | WO 2014/121293 | 8/2014 |
| WO | WO 2015/168329 | 11/2015 |

OTHER PUBLICATIONS

Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.

International Preliminary Report on Patentability re App. No. PCT/US2010/056620, issued May 15, 2012. in 10 pages.

International Search Report and Written Opinion from International Application No. PCT/US2011/057401, Jan. 30, 2012, in 20 pages.

Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.

Al-Jadaa et al; Acoustic Hypochlorite Activation in Simulated Curved Canals; pp. 1408-1411; Journal of Endodontics, vol. 35, No. 10; Oct. 2009.

Anand et al; Prevention of Nozzle Wear in High-Speed Slurry Jets Using Porous Lubricated Nozzles; pp. 1-13; Department of Mechanical Engineering, The Johns Hopkins University, Oct. 2000.

Anantharamaiah et al; A simple expression for predicting the inlet roundness of micro-nozzles; pp. N31-N39; Journal of Micromechanics and Microengineering, vol. 17; Mar. 21, 2007.

Anantharamaiah et al; A study on flow through hydroentangling nozzles and their degradation; pp. 4582-4594; Chemical Engineering Science, vol. 61; May 2006.

Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.

Attin et al; Clinical evaluation of the cleansing properties of the nonistrumental technique for cleaning root canals; pp. 929-933; International Endodontic Journal, vol. 35, Issue 11; Nov. 2002.

Batchelor et al; Analysis of the stability of axisymmetric jets; pp. 529-551; Journal of Fluid Mechanics, vol. 14; Dec. 1962.

Begenir et al; Effect of Nozzle Geometry on Hydroentangling Water Jets: Experimental Observations; pp. 178-184; Textile Research Journal, vol. 74; Feb. 2004.

Begenir, Asli; The Role of Orifice Design in Hydroentanglement; Thesis submitted to North Carolina State University; dated Dec. 2002, in 107 pages.

Borkent et al; Is there gas entrapped on submerged silicon wafers? Visualizing nano-scale bubbles with cavitation; pp. 225-228; Solid State Phenomena, vol. 134 (2008); available online Nov. 2007.

Bremond et al; Cavitation on surfaces; pp. S3603-S3608; Journal of Physics: Condensed Matter, vol. 17; Oct. 28, 2005.

Brennen, Christopher E.; Fission of collapsing cavitation bubbles; pp. 153-166; Journal of Fluid Mechanics, vol. 472; Dec. 2002.

Chang et al; Effects of Inlet Surface Roughness, Texture, and Nozzle Material on Cavitation; pp. 299-317; Atomization and Sprays, vol. 16 (2006).

Culjat et al., "B-Scan Imaging of Human Teeth Using Ultrasound," Apr. 2003, in 4 pages.

Didenkulov et al; Nonlinear Acoustic Diagnostics of Scatterer Spatial Distribution in a Cavitation Jet; Nov. 19-23, 2001, pp. 276-278, XI Session of the Russion Acoustical Society.

Dumouchel, Christophe; On the experimental investigation on primary atomization of liquid streams; pp. 371-422; Experimental Fluids, vol. 45; Jun. 22, 2008.

Eddingfield et al; Mathematical Modeling of High Velocity Water Jets; pp. 25-39; Proceedings of 1st U.S. Water Jet Conference; 1981.

EMS Electro Medical Systems, "Cleaning", in 2 pages, dated 2005, downloaded from http://www.ems-dent.com/en/endodontics cleaning. htm.

ESI Endo Soft Instruments, EMS Electro Medical Systems, Brochure in 2 pages, downloaded from www.emsdent.com, dated Jan. 2004.

Feng et al; Enhancement of ultrasonic cavitation yield by multi-frequency sonication; pp. 231-236; Ultrasonics Sonochemistry, vol. 9; Oct. 2002.

Foldyna et al; Acoustic wave propagation in high-pressure system; pp. e1457-e1460; Ultrasonics vol. 44 (Supplement 1); Jun. 8, 2006.

G.E. Reisman and C.E. Brennen, "Pressure Pulses Generated by Cloud Cavitation", FED-vol. 236, 1996 Fluids Engineering Division Conference, vol. 1, pp. 319-328, ASME 1996.

G.E. Reisman, Y.-C. Wang and C.E. Brennen, "Observations of shock waves in cloud cavitation", J. Fluid Mech. (1998), vol. 355, pp. 255-283.

Ghassemieh et al; Effect of Nozzle Geometry on the Flow Characteristics of Hydroentangling Jets; pp. 444-450; Textile Research Journal, vol. 73; May 2003.

Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.

Hahn et al; Acoustic resonances in the bubble plume formed by a plunging water jet; pp. 1751-1782; Proceedings of the Royal Society of London A, vol. 459; May 16, 2003.

Hashish, Mohamed; Experimental Studies of Cutting with Abrasive Waterjets; pp. 402-416; Proceedings of 2nd American Water Jet Conference; 1983.

Herbert et al; Cavitation pressure in water; pp. 041603-1 to 041603-22; Physical Review E, vol. 74; Oct. 2006.

Hiroyasu, Hiro; Spray Breakup Mechanism from the Hole-Type Nozzle and its Applications; pp. 511-527; Atomization and Sprays, vol. 10 (2000).

Hoque et al; Air entrainment and associated energy dissipation in steady and unsteady plunging jets at free surface; pp. 37-45; Applied Ocean Research, vol. 30; May 2008.

Hydrocision Products: SpineJet Hydrosurgery; system webpage in 2 pages, copyright 2010, downloaded from http://www.hydrocision.com on Apr. 22, 2010.

Hydrocision SpineJet XL HydroSurgery System; Brochure in 2 pages, copyright 2004-2006, downloaded from http://www.hydrocision.com on Apr. 22, 2010.

International Preliminary Report and Written Opinion dated Nov. 9, 2010 for International Appl. No. PCT/US09/43386.

International Preliminary Report on Patentability dated Aug. 6, 2009, for International Appl. No. PCT/US08/52122.

International Preliminary Report on Patentability dated Oct. 30, 2008, for International Appl. No. PCT/US07/09633.

International Search Report and Written Opinion dated Apr. 11, 2008, for International Appl. No. PCT/US07/09633.

(56) References Cited

OTHER PUBLICATIONS

International Search Report and Written Opinion dated Aug. 8, 2008, for International Appl. No. PCT/US08/52122.
International Search Report and Written Opinion dated Jul. 29, 2009, for International Appl. No. PCT/US09/43386.
International Search Report and Written Opinion re App. No. PCT/US2010/056620, dated Jan. 12, 2011.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; In CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc ., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
Flint, E. B., et al., "The Temperature of Cavitation", Science, vol. 253, Sep. 20, 1991, pp. 1397-1399.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
European Extended Search Report received in European Patent Application No. 09743801.4, dated Jun. 4, 2012; in 5 pages.
International Preliminary Report on Patentability received in International Patent Application No. PCT/US2011/057401, mailed on Jan. 25, 2013, filed on Oct. 21, 2011; in 13 pages.
Fuchs, "Ultrasonic Cleaning: Fundamental Theory and Application," Blackstone-Ney Ultrasonics, Jamestown, NY, May 2002.
Hungarian Written Opinion and Search Report via/re Singapore Application No. 189554, mailed Oct. 13, 2013.
International Search Report and Written Opinion mailed Jun. 28, 2013, re PCT Application No. PCT/US2013/036493, in 21 pages.
Sabeti, "Healing of apical periodontitis after endodontic treatment with and without obturation in dogs," Journal of Endodontics, Jul. 2006, pp. 628-633.
International Search Report and Written Opinion, re PCT Application No. PCT/US13/32635, mailed Jun. 17, 2013, in 13 pages.
International Preliminary Report on Patentability and Written Opinion, mailed Oct. 14, 2014, re PCT Application No. PCT/US2013/036493, in 14 pages.
European Extended Search Report, re EP Application No. 08728345.3, dated Mar. 3, 2014.
International Search Report and Written Opinion re App. No. PCT/US2014/014732, mailed Jul. 18, 2014.
International Search Report and Written Opinion, re PCT Application No. PCT/US2013/077286, mailed May 27, 2014.
Japanese Office Action, re JP Application No. 2012-539042, mailed Aug. 5, 2014.
European Exam Report, dated Jun. 11, 2015, for EP Application No. 07755777.5, in 6 pages.

(56) References Cited

OTHER PUBLICATIONS

European Extended Search Report re EP Application No. 14187012.1, dated Mar. 3, 2015, in 10 pages.
International Preliminary Report on Patentability re PCT Application No. PCT/US2014/014732, issued Aug. 4, 2015.
International Preliminary Report on Patentability, re PCT Application No. PCT/US2013/077286, issued Jun. 23, 2015.
International Search Report and Written Opinion, re PCT Application No. PCT/US2014/036451, mailed Jan. 21, 2015, in 20 pages.
International Search Report and Written Opinion, re PCT Application No. PCT/US2014/044186, mailed Jan. 21, 2015, in 19 pages.
European Extended Search Report, re EP Application No. 10830829.7, dated Oct. 21, 2015.
European Extended Search Report, re EP Application No. 13775073.3, dated Nov. 3, 2015.
International Preliminary Report on Patentability, re PCT Application No. PCT/US2014/036451, issued Nov. 3, 2015, 2015, in 11 pages.
International Search Report and Written Opinion, re PCT Application No. PCT/US2015/028360, mailed Sep. 28, 2015.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
European Extended Search Report, re EP Application No. 11835265.7, dated Mar. 30, 2016, in 9 pages.
European Extended Search Report, re EP Application No. 13763534.8, dated Jan. 15, 2016.
International Preliminary Report on Patentability, re PCT Application No. PCT/US2014/044186, mailed Dec. 29, 2015, in 19 pages.
Wohlemuth et al.: "Effectiveness of GentleWave System in Removing Separated Instruments," Joe, vol. 41, No. 11, Nov. 2015.

* cited by examiner

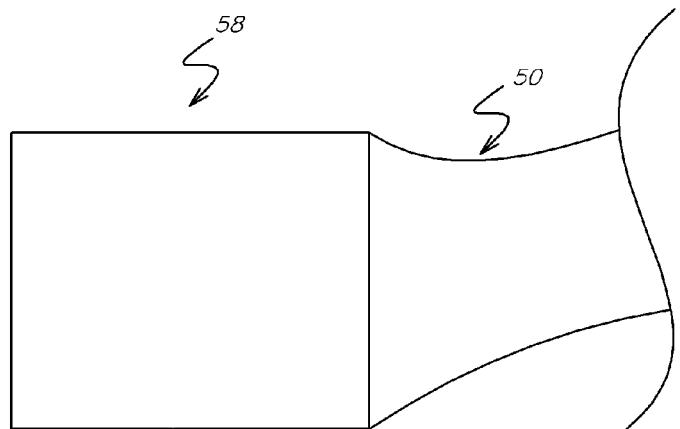
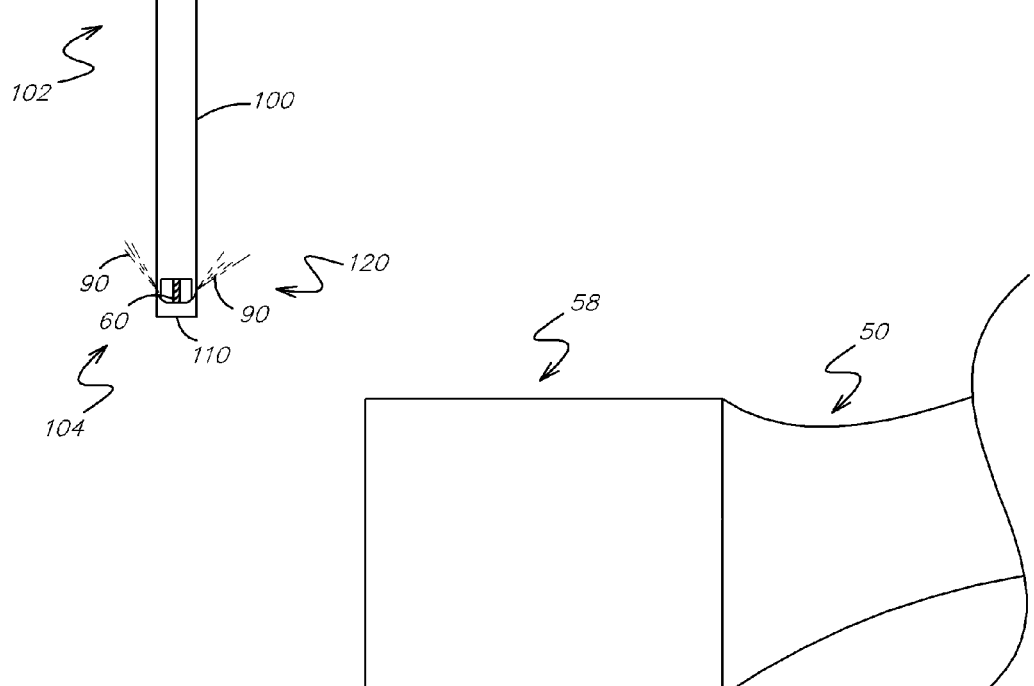
FIG. 7A
FIG. 7B

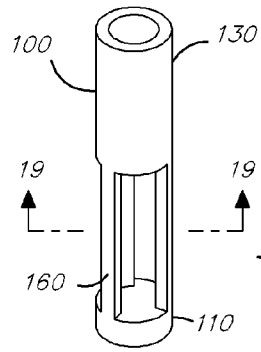
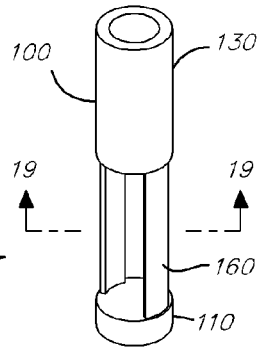
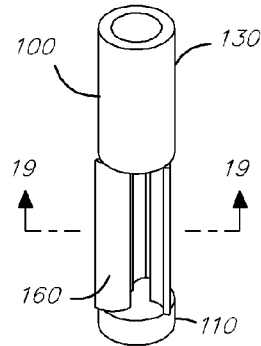
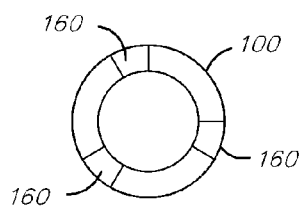
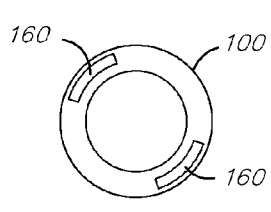
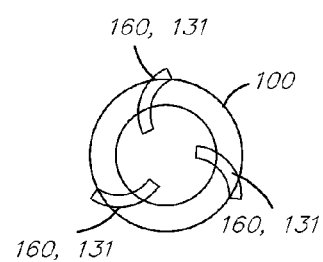
FIG. 19A          FIG. 19B          FIG. 19C
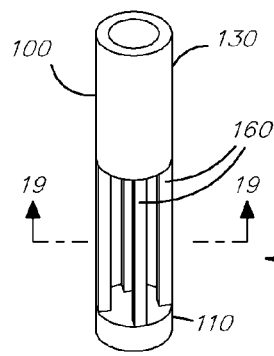
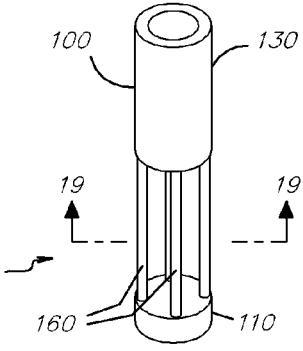
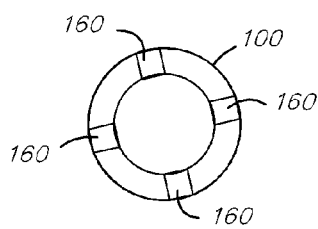
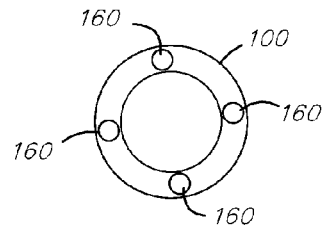
FIG. 19D          FIG. 19E

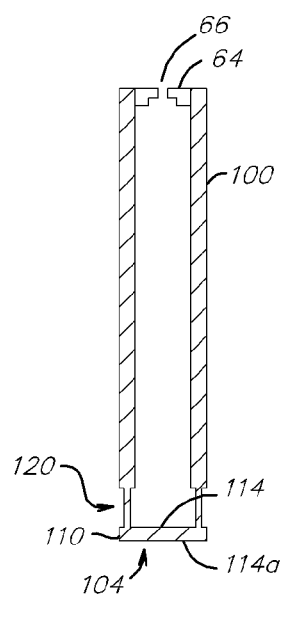
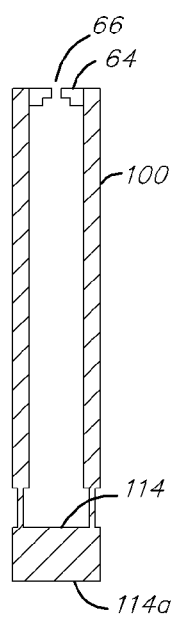
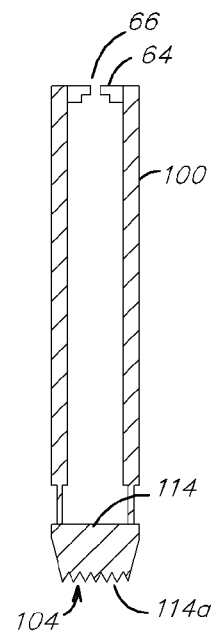
FIG. 24A     FIG. 24B     FIG. 24C
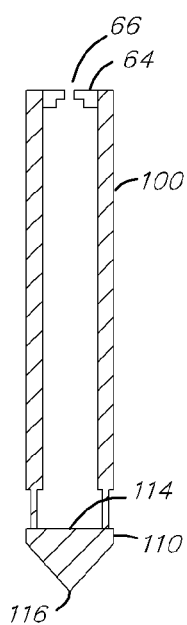
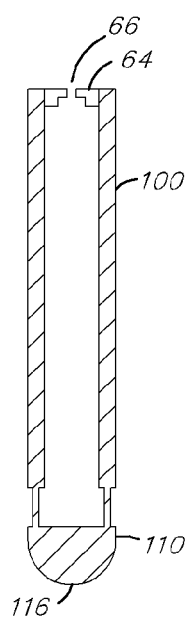
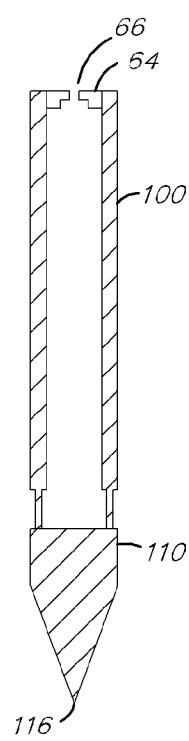
FIG. 24D     FIG. 24E     FIG. 24F

LIQUID JET APPARATUS AND METHODS FOR DENTAL TREATMENTS

CROSS-REFERENCE TO RELATED APPLICATIONS

This application claims the benefit under 35 U.S.C. §119 (e) of U.S. Provisional Patent Application No. 61/261,293, filed Nov. 13, 2009, entitled "APPARATUS AND METHODS FOR ROOT CANAL TREATMENTS," which is hereby incorporated by reference herein in its entirety and made part of this specification.

BACKGROUND

1. Field

The present disclosure generally relates to methods and apparatus for treatment of a tooth and, more particularly, methods and apparatus using liquid jets for removing organic matter from a tooth.

2. Description of the Related Art

In conventional root canal procedures, an opening is drilled through the crown of a diseased tooth, and endodontic files are inserted into the root canal system to open the canal spaces and remove organic material therein. The root canal is then filled with solid matter such as gutta percha or a flowable obturation material, and the tooth is restored. However, this procedure will not remove all organic material from the canal spaces, which can lead to post-procedure complications such as infection. In addition, motion of the endodontic file may force organic material through an apical opening into periapical tissues. In some cases, an end of the endodontic file itself may pass through the apical opening. Such events may result in trauma to the soft tissue near the apical opening and lead to post-procedure complications.

SUMMARY

Various non-limiting aspects of the present disclosure will now be provided to illustrate features of the disclosed apparatus and methods.

In one aspect, a dental instrument comprises a positioning member having a channel configured to deliver a high-velocity liquid jet to a cavity in a tooth. The positioning member may have a proximal end portion and a distal end portion. The distal end portion may be configured to direct the liquid jet into the cavity in the tooth. In one embodiment, the positioning member may comprise an elongated member such as, e.g., a guide tube.

In another aspect, the dental instrument may include a backflow restrictor that is configured to be applied to the tooth. The backflow restrictor may be configured to inhibit backflow of fluid out of an opening in the tooth during operation of the liquid jet. At least a portion of the backflow restrictor may be disposed between the proximal end portion and the distal end portion of the positioning member.

In another aspect, a method for treatment of a root canal of a tooth is described. The method comprises disposing an impingement member having an impingement surface, separate from a tooth, in a cavity in the tooth. The method also comprises generating a high-velocity, coherent, collimated liquid jet, and directing the jet through air toward the cavity such that liquid enters the cavity in the tooth and fills at least a substantial portion of the cavity. The method also comprises impacting the jet on the impingement surface, and passing the jet through at least a portion of the liquid filling the at least a substantial portion of the cavity prior to the impacting.

In another aspect, a method for treatment of a root canal in a tooth is disclosed. The method comprises generating a high-velocity liquid beam with a nozzle disposed in an interior of a tooth, and impacting an impingement surface disposed in a fluid environment located in the interior of the tooth with the high-velocity liquid beam.

For purposes of this summary, certain aspects, advantages, and novel features of the inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein.

BRIEF DESCRIPTION OF THE DRAWINGS

FIGS. 7A-7B are side views schematically illustrating embodiments of the distal ends of handpieces comprising embodiments of guide tubes.

FIG. 17A is a side view along the line A-A shown in FIG. 17B. FIG. 17C is a side view along the line C-C shown in FIG. 17D.

FIGS. 19A-19E each include a perspective view (upper figure) and a cross-section view (lower figure) taken along the line 19-19 of the upper figure schematically illustrating an embodiment of a guide tube.

FIGS. 24A-24F are cross-section views schematically illustrating embodiments of guide tubes.

Figure 1:
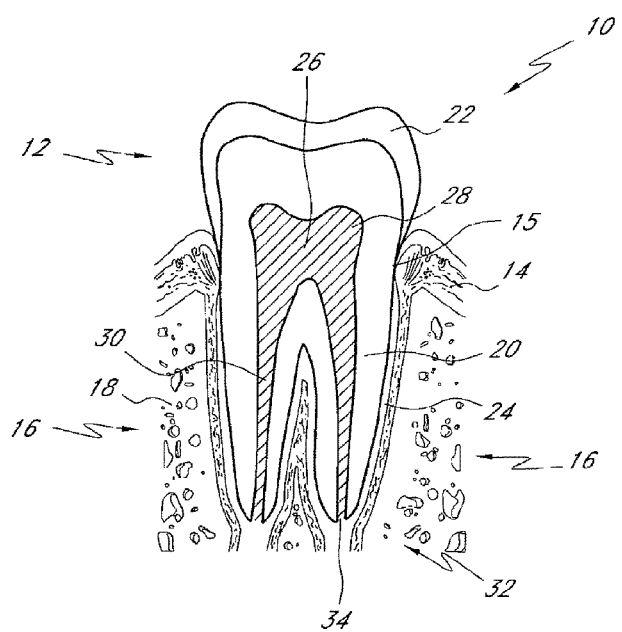
FIG. 1 is a cross-section view schematically illustrating a root canal system of a tooth.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

Overview

The present disclosure describes apparatus and methods for performing dental procedures such as, e.g., endodontic procedures. The disclosed apparatus and methods advantageously may be used with root canal cleaning treatments, for example, to efficiently remove organic and/or inorganic matter from a root canal system. The apparatus and methods may be used for other dental treatments such as, e.g., tooth cleaning, treatment of dental caries, removal of calculus and plaque, etc. Organic material (or organic matter) includes organic substances typically found in healthy or diseased teeth or root canal systems such as, for example, soft tissue, pulp, blood vessels, nerves, connective tissue, cellular matter, pus, and microorganisms, whether living, inflamed, infected, diseased, necrotic, or decomposed. Inorganic matter includes calcified tissue and calcified structures, which are frequently present in the root canal system.

In some embodiments, the disclosed apparatus and methods utilize a high-velocity collimated beam of liquid to clean the root canal system, to clean tooth surfaces (e.g., to treat dental caries), etc. The high-velocity liquid beam may generate a pressure wave that can propagate through the tooth and root canal system and can detach or dissolve organic and/or inorganic material from dentinal surfaces and/or dissociate pulpal tissue. The liquid beam and/or the pressure wave may cause or increase the efficacy of various effects that may occur in the tooth including, but not limited to, acoustic cavitation (e.g., bubble formation and collapse, microjet formation), fluid agitation, fluid circulation, sonoporation, sonochemistry, and so forth.

For example, in one aspect of the disclosure, an apparatus for removing organic and/or inorganic material from a tooth comprises a pressure wave generator configured to provide acoustic energy to a tooth. The acoustic energy may be sufficient to cause organic and/or inorganic material in the tooth to be detached from surrounding dentin. It is believed (although not required) that the effects caused (or enhanced) by the acoustic energy may lead to a cleaning action that delaminates or detaches the pulpal tissue from the root canal wall, dentinal surfaces, and/or tubules, and may further break such tissue down into smaller pieces.

In some implementations, the pressure wave generator comprises embodiments of the apparatus described herein. For example, the pressure wave generator may comprise a positioning member (e.g., a guide tube) having a channel or lumen along which or through which a liquid jet can propagate. The distal end portion of the positioning member may include an impingement surface on which the liquid jet impinges and is deflected into jets or spray. The distal end portion of the positioning member may include one or more openings that permit the deflected liquid to exit the positioning member and interact with the surrounding environment in the tooth. In some treatment methods, the openings disposed at or near the distal end portion of the positioning member are submerged in liquid in the tooth. Without subscribing to or being limited by any particular theory or mode of operation, the flow of the submerged portion of the liquid jet may generate a cavitation cloud within the treatment fluid. The creation and collapse of the cavitation cloud and/or the jet impacting the impingement surface may, in some cases, generate a substantial hydroacoustic field in the tooth. This acoustic field may generate pressure waves, oscillations, and/or vibrations in or near the canal spaces of the tooth and/or interior dentinal surfaces, which are filled with dentinal tubules. Further cavitation effects may be possible, including growth, oscillation, and collapse of cavitation bubbles formed in or near the tubules (e.g., possibly at the high surface-energy sites of the tubules). These (and/or other) effects may lead to efficient cleaning of the pulp cavity of the tooth. In some implementations, the pressure wave generator may be coupled to a handpiece or portable jet housing that may be maneuvered in the mouth of the patient so as to position or orient the pressure wave generator relative to a desired tooth under treatment.

Example Embodiments of Apparatus and Methods for Dental Treatments

FIG. 1 is a cross section schematically illustrating a typical human tooth 10, which comprises a crown 12 extending above the gum tissue 14 and at least one root 16 set into a socket (alveolus) within the jaw bone 18. Although the tooth 10 schematically depicted in FIG. 1 is a molar, the apparatus and methods described herein may be used on any type of tooth such as an incisor, a canine, a bicuspid, or a molar. The hard tissue of the tooth 10 includes dentin 20 which provides the primary structure of the tooth 10, a very hard enamel layer 22 which covers the crown 12 to a cementoenamel junction 15 near the gum 14, and cementum 24 which covers the dentin 20 of the tooth 10 below the cementoenamel junction 15.

A pulp cavity 26 is defined within the dentin 20. The pulp cavity 26 comprises a pulp chamber 28 in the crown 11 and a root canal space 30 extending toward an apex 32 of each root 16. The pulp cavity 26 contains dental pulp, which is a soft, vascular tissue comprising nerves, blood vessels, connective tissue, odontoblasts, and other tissue and cellular components. The pulp provides innervation and sustenance to the tooth through the epithelial lining of the pulp chamber 26 and the root canal space 30. Blood vessels and nerves enter/exit the root canal space 30 through a tiny opening, the apical foramen 32, near a tip of the apex 32 of the root 16.

Figure 2:
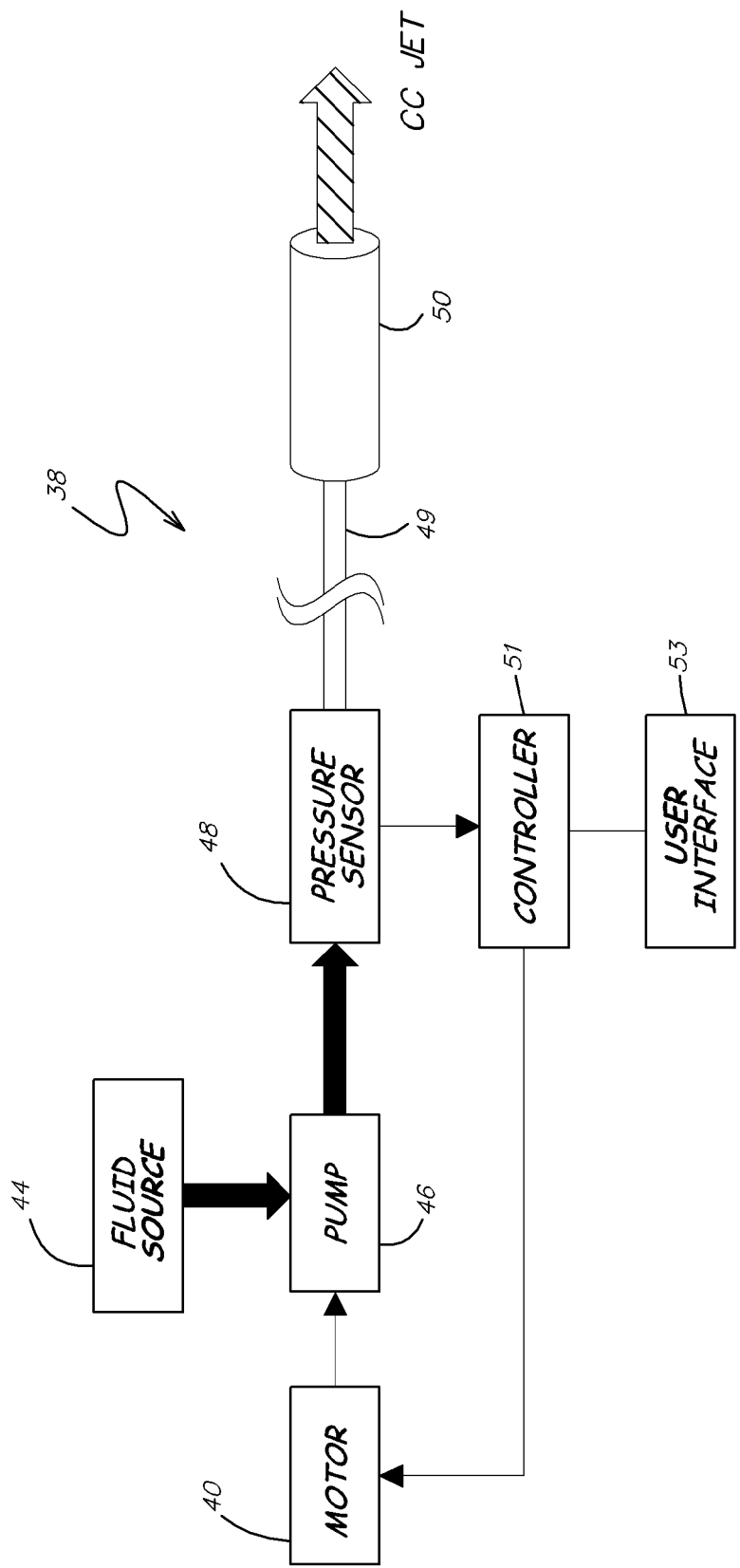
FIG. 2 is a block diagram schematically illustrating an embodiment of a system adapted to produce a high-velocity liquid jet.

FIG. 2 is a block diagram that schematically illustrates an embodiment of a system 38 adapted to generate a high-velocity jet 60 of fluid for use in dental procedures. The system 38 comprises a motor 40, a fluid source 44, a pump 46, a pressure sensor 48, a controller 51, a user interface 53, and a handpiece 50 that can be operated by a dental practitioner to direct the jet 60 toward desired locations in a patient's mouth. The pump 46 can pressurize fluid received from the fluid source 44. The pump 46 may comprise a piston pump in which the piston is actuatable by the motor 40. The high-pressure liquid from the pump 46 can be fed to the pressure sensor 48 and then to the handpiece 50, for example, by a length of high-pressure tubing 49. The pressure sensor 48 may be used to sense the pressure of the liquid and communicate pressure information to the controller 51. The controller 51 can use the pressure information to make adjustments to the motor 40 and/or the pump 46 to provide a target pressure for the fluid delivered to the handpiece 50. For example, in embodiments in which the pump 46 comprises a piston pump, the controller 51 may signal the motor 40 to drive the piston more rapidly or more slowly, depending on the pressure information from the pressure sensor 48. In some embodiments, the pressure of the liquid that can be delivered to the handpiece 50 can be adjusted within a range from about 500 psi to about 50,000 psi (1 psi is 1 pound per square inch and is about 6895 Pascals (Pa)). In certain embodiments, it has been found that a pressure range from about 2,000 psi to about 15,000 psi produces jets that are particularly effective for endodontic treatments. In some embodiments, the pressure is about 10,000 psi.

The fluid source 44 may comprise a fluid container (e.g., an intravenous bag) holding sterile water, a medical-grade saline solution, an antiseptic or antibiotic solution (e.g., a bleach such as sodium hypochlorite), a solution with chemicals or medications, or any combination thereof. More than one fluid source may be used. In certain embodiments, it is advantageous for jet formation if the liquid provided by the fluid source 44 is substantially free of dissolved gases (e.g., less than about 0.1% by volume, less than about 1 mg of gas per liter of solution, or less than some other value), which may reduce the acoustic effects of cavitation. In some embodiments, the fluid source 44 comprises degassed distilled water. A bubble detector (not shown) may be disposed between the fluid source 44 and the pump 46 to detect bubbles in the liquid and/or to determine whether liquid flow from the fluid source 44 has been interrupted or the container has emptied. The liquid in the fluid source 44 may be at room temperature or may be heated and/or cooled to a different temperature. For example, in some embodiments, the liquid in the fluid source 44 can be chilled to reduce the temperature of the high velocity jet generated by the system 38, which may reduce or control the temperature of the fluid inside a tooth. In some treatment methods, the liquid in the fluid source 44 can be heated, which may increase the rate of chemical reactions that may occur in the tooth during treatment.

The handpiece 50 can be configured to receive the high pressure liquid and can be adapted at a distal end to generate a high-velocity beam or jet 60 of liquid for use in dental procedures. In some embodiments, the system 38 may produce a coherent, collimated jet of liquid (further described below). The handpiece 50 may be sized and shaped to be maneuverable in the mouth of a patient so that the jet 60 may be directed toward or away from various portions of the tooth 10. In some embodiments, the handpiece comprises a housing or cap that can be coupled to the tooth 10.

The controller 51 may comprise a microprocessor, a special or general purpose computer, a floating point gate array, and/or a programmable logic device. The controller 51 may be used to control safety of the system 38, for example, by limiting system pressures to be below safety thresholds and/or by limiting the time that the jet 60 is permitted to flow from the handpiece 50. The system 38 may also include a user interface 53 that outputs relevant system data or accepts user input (e.g., a target pressure). In some embodiments, the user interface 53 comprises a touch screen graphics display. In some embodiments, the user interface 53 may include controls for a dental practitioner to operate the liquid jet apparatus. For example, the controls can include a foot switch to actuate or deactuate the jet.

The system 38 may include additional and/or different components and may be configured differently than shown in FIG. 2. For example, the system 38 may include an aspiration pump that is coupled to the handpiece 50 (or an aspiration cannula) to permit aspiration of organic matter from the mouth or tooth 10. In other embodiments, the system 38 may comprise other pneumatic and/or hydraulic systems adapted to generate the high-velocity beam or jet 60. Also, certain embodiments of the system 38 may utilize or be configured similarly to embodiments of the apparatus and systems described in U.S. Pat. No. 6,224,378, issued May 1, 2001, entitled "METHOD AND APPARATUS FOR DENTAL TREATMENT USING HIGH PRESSURE LIQUID JET," U.S. Pat. No. 6,497,572, issued Dec. 24, 2002, entitled "APPARATUS FOR DENTAL TREATMENT USING HIGH PRESSURE LIQUID JET," U.S. Patent Publication No. 2007/0248932, published Oct. 25, 2007, entitled "APPARATUS AND METHODS FOR TREATING ROOT CANALS OF TEETH," and/or U.S. Patent Publication No. 2010/0143861, published Jun. 10, 2010, entitled "APPARATUS AND METHODS FOR MONITORING A TOOTH," the entire disclosure of each of which is hereby incorporated by reference herein for all that it teaches or discloses.

In certain embodiments, the system 38 may be configured to produce a liquid jet 60 that forms a substantially parallel beam (e.g., is "collimated") over distances ranging from about 0.01 cm to about 10 cm. In some embodiments, the velocity profile transverse to the propagation axis of the jet is substantially constant (e.g., is "coherent"). For example, in some implementations, away from narrow boundary layers near the outer surface of the jet 60 (if any), the jet velocity is substantially constant across the width of the jet. Therefore, in certain advantageous embodiments, the liquid jet 60 delivered by the dental handpiece 50 may comprise a coherent, collimated jet (a "CC jet"). In some implementations, the CC jet may have velocities in a range from about 100 m/s to about 300 m/s, for example, about 190 m/s in some embodiments. In some implementations, the CC jet can have a diameter in a range from about 5 microns to about 1000 microns, in a range from about 10 microns to about 100 microns, in a range from about 100 microns to about 500 microns, or in a range from about 500 microns to about 1000 microns. Further details with respect to CC jets that can be produced by embodiments of the system and apparatus described herein can be found in U.S. Patent Publication No. 2007/0248932, which is hereby incorporated by reference herein in its entirety for all that it discloses or teaches.

Figure 3:
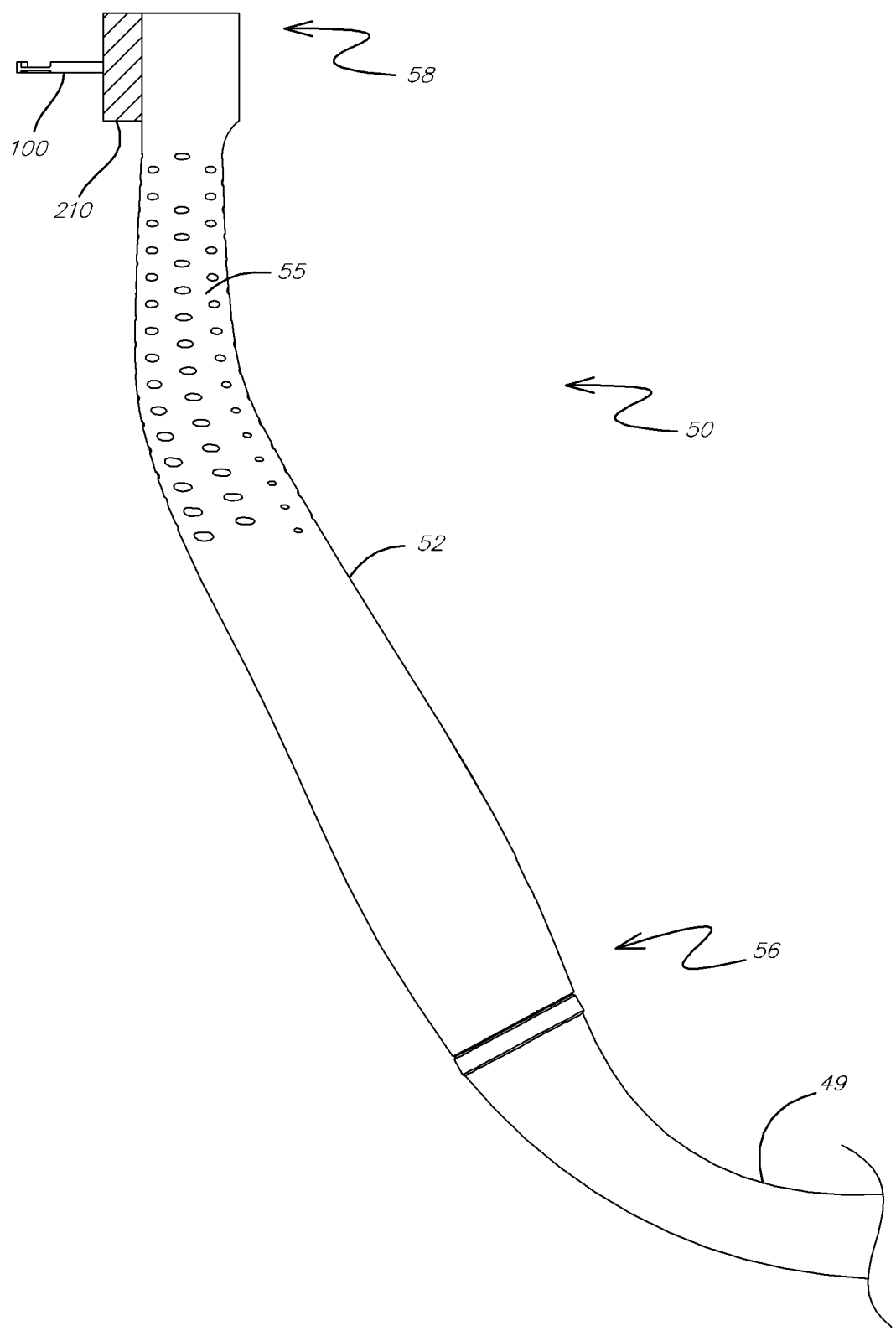
FIG. 3 is a side view schematically illustrating an embodiment of a handpiece comprising an embodiment of a guide tube for delivery of the liquid jet to a portion of a tooth.

FIG. 3 is a side view schematically illustrating an embodiment of a handpiece 50 comprising an embodiment of a positioning member configured to deliver the liquid jet 60 to a portion of the tooth 10. In various embodiments, the positioning member comprises a guide tube 100. Embodiments of the handpiece 50 can be used with any of the embodiments of the guide tubes 100 described herein. The handpiece 50 comprises an elongated tubular barrel 52 having a proximal end 56 that is adapted to engage tubing 49 from the system 38. The barrel 52 may include features or textures 55 that enhance grasping the handpiece 50 with the fingers and thumb of the operator. The handpiece 50 can be configured to be handheld. In some cases, the handpiece 50 can be configured to be portable, movable, orientable, or maneuverable with respect to the patient. In some implementations, the handpiece 50 can be configured to be coupled to a positioning device (e.g., a maneuverable or adjustable arm).

The handpiece 50 can be shaped or sized differently than shown in FIG. 3 (or other figures herein). For example, the handpiece 50 can comprise a housing or cap that can be coupled to the tooth 10. In some such implementations, the elongated tubular barrel 52 may not be used, and a dental practitioner maneuvers the housing into a desired location in the patient's mouth.

Optionally, a flow restrictor 210 can be disposed at the distal end 58 of the handpiece 50. In the illustrated embodiment, the flow restrictor 210 substantially surrounds the guide tube 100. As will be further described with reference to FIG. 25, the flow restrictor 210 may be configured to contact a portion of the tooth 10 during a dental treatment and may restrict, inhibit, or reduce backflow of fluid out of the tooth during treatment.

Figure 4:
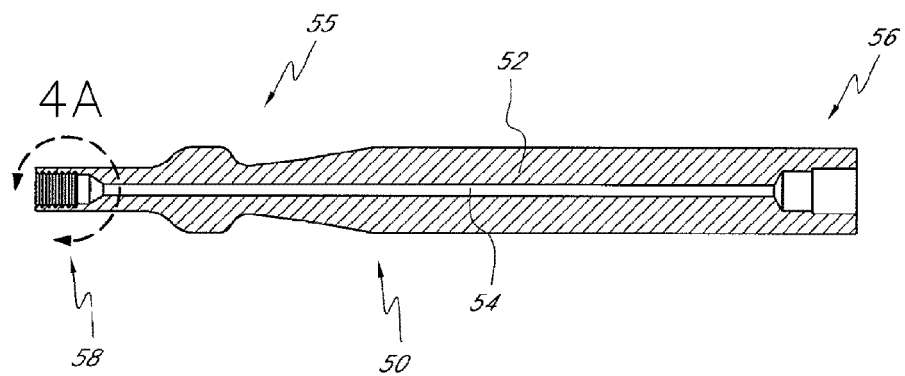
FIGS. 4 and 4A are cross-section views schematically illustrating another embodiment of a handpiece that can be used to deliver the high-velocity liquid jet.
Figure 4A:
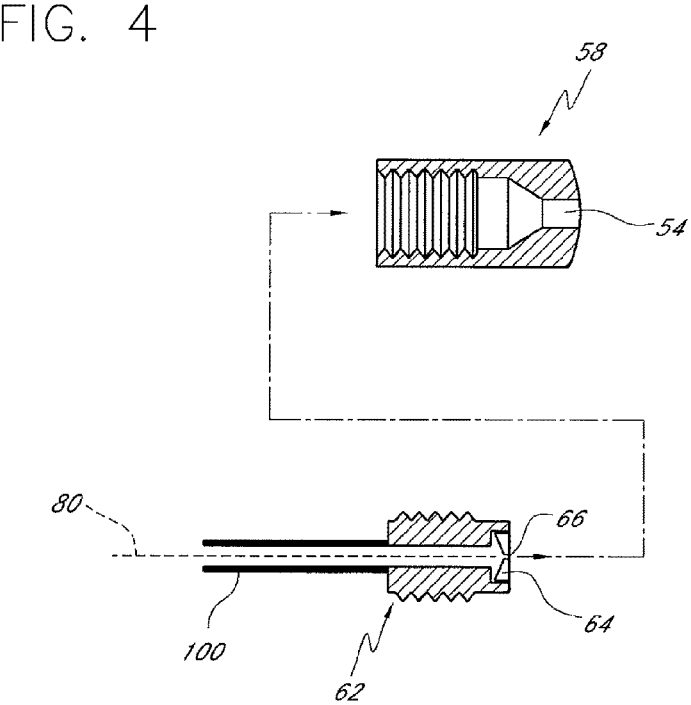

FIGS. 4 and 4A are cross-section views that schematically illustrate another embodiment of a handpiece 50 adapted for delivering the high-velocity jet 60. The handpiece 50 has a central passageway 54 extending axially therethrough and at the proximal end 56 is adapted to engage the tubing 49 from the system 38 in order for the passageway 54 to be in fluid communication with the high pressure liquid delivered by the system 38. A distal end 58 of the barrel 52 (shown in close-up in FIG. 4A) includes a threaded recess adapted to engage complementary threads of a nozzle mount 62, which is configured to hold a nozzle 64. The nozzle mount 62 may be tightly screwed into the distal end 58 of the barrel 52 to secure the nozzle 64 adjacent to a distal end of the passageway 52. As will be described with reference to FIGS. 11A-11C, the nozzle 64 can be disposed in different locations in other embodiments of the handpiece.

FIG. 4A schematically illustrates an embodiment of a guide tube 100 secured to the nozzle mount 62. In some embodiments, the guide tube 100 can be formed integrally with the nozzle mount 62. In other embodiments, the guide tube 100 can be secured to the nozzle mount 62 via welding (e.g., laser welding), adhesives, fasteners, etc. Embodiments of the guide tube 100 can be manufactured using a variety of process including, e.g., metal injection molding, laser cutting or welding, micro welding, etc. Various embodiments of the guide tube 100 will be further described below. In some implementations, the handpiece 50 may be configured to deliver two or more jets, and in some such embodiments, two or more nozzles 62 and/or guide tubes 100 may be disposed at the distal end 58 of the handpiece 50.

The nozzle 64 can comprise a circular, disc-like element having an orifice 66 formed therein. The nozzle 64 may be fabricated from a suitably rigid material that resists deformation under high pressure such as, for example, metal, ceramic, or synthetic sapphire or ruby. Embodiments of the nozzle 64 can be manufactured by a variety of processes including, e.g., electroforming (including nickel-cobalt electroforms), micro-plunge electrical discharge machining (EDM), laser cutting, etc.

In the illustrated embodiment, the nozzle mount 62 secures the nozzle 64 substantially perpendicular to the passageway 54 so that high pressure liquid in the passageway 54 can flow through the orifice 66 and emerge as a highly collimated beam of fluid traveling along a longitudinal jet axis 80 that is substantially coaxial with the barrel 52 of the handpiece 50. The orifice 66 may have any desired shape such as, e.g., circular, oval, rectangular, polygonal, etc. The orifice 66 may, but need not be, substantially centered in the nozzle 64. In some embodiments, the nozzle 64 may have two or more orifices 66, with each orifice configured to emit a liquid jet. In some embodiments, the distal end 58 of the handpiece 50 may include additional components, for example, to assist guiding or directing the jet 60 and/or to provide aspiration.

Various aspects of the nozzle 64 (e.g., surface finish of the orifice) may be selected to provide desired fluid flow or jet properties. For example, in various embodiments, the liquid jet emitted from the orifice 66 can be a CC jet, a jet with a perturbed surface, or a spray of fluid (as measured in air). Without subscribing to or requiring any particular theory or mode of operation, it is believed that a nozzle 64 configured to produce a CC jet may create a higher power acoustic field (e.g., pressure waves) in a tooth (e.g., in dentin or in liquid in the pulp cavity) than a nozzle 64 that is configured not to produce a CC jet. For example, it is believed that a CC-Jet may create a large velocity gradient that may result in a large pressure gradient that may cause stronger cavitation, which may cause a higher power acoustic field. Therefore, in some treatment methods, a system configured to produce a CC jet may be used for root canal cleaning, and in other treatment methods, system configured to produce a non-CC jet may be used for tooth cleaning (e.g., caries treatment, removal of calculus and plaque, superficial cleaning, etc.).

Figure 5A:
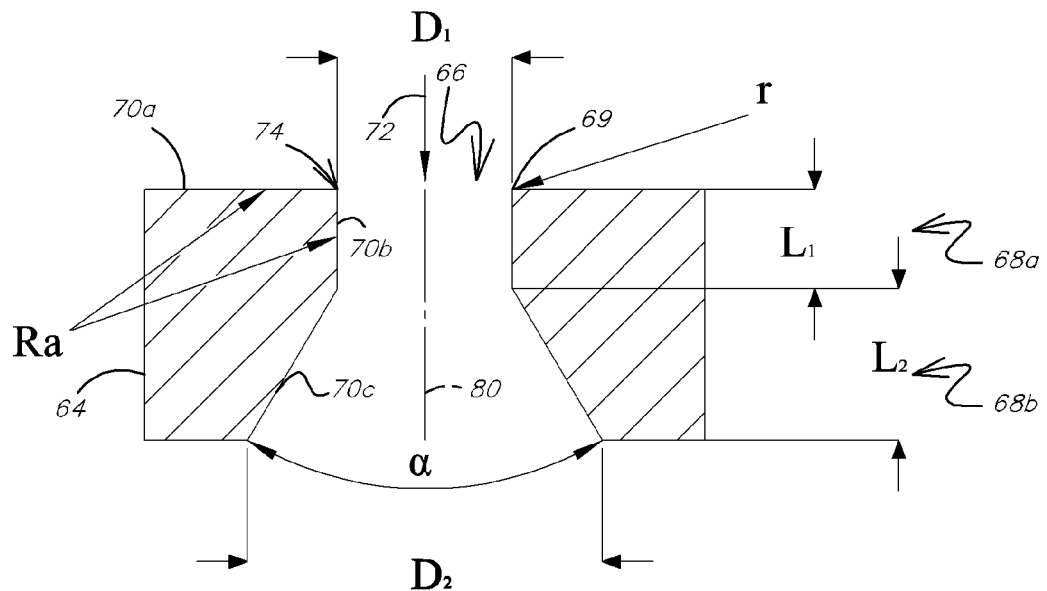
FIGS. 5A and 5B are cross-section views that schematically illustrate embodiments of a nozzle having an orifice.
Figure 5B:
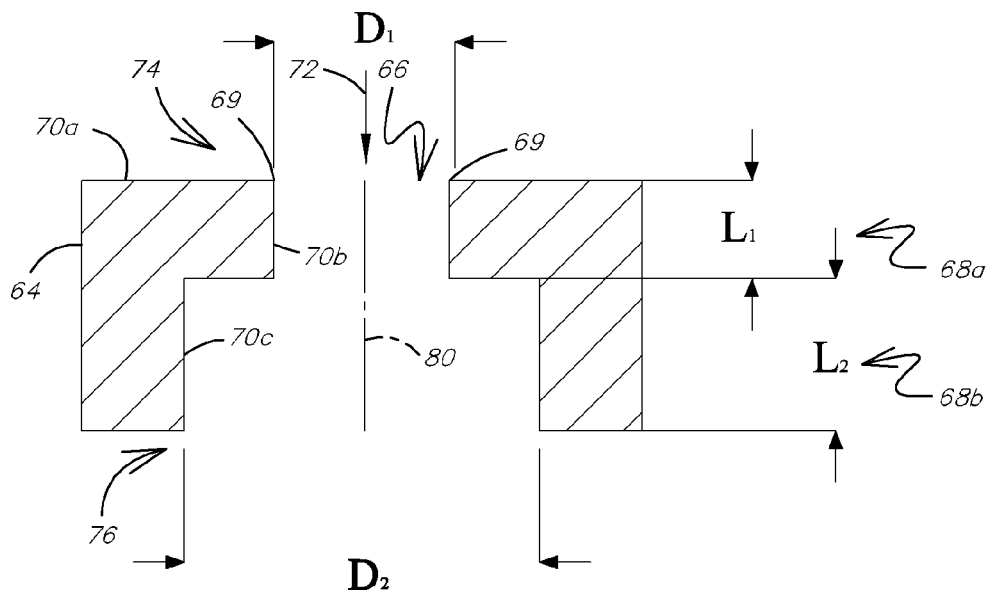

Different types of fluid streams (e.g., a jet or a spray) can be generated by the nozzle 64 and/or orifice 66 based at least in part on flow parameters, nozzle geometry, surface quality of the orifice 66 (or other surfaces in the nozzle 64), and so forth. FIGS. 5A and 5B are cross-section views that schematically illustrate embodiments of a nozzle 64 having an orifice 66. Nozzles and/or orifices can be configured in a number of ways to provide a CC jet. For example, as schematically illustrated in FIG. 5A, in some embodiments a relatively sharp-edged, cone-down orifice 66 can be used. In other embodiments, other shapes can be used, e.g., conical orifices, capillary orifices, cone-capillary orifices, etc. Arrow 72 shows the direction of fluid flow through the orifice 66 during operation of the liquid jet apparatus.

In the illustrated embodiments, the orifice 66 is substantially circularly symmetric, although this is not a requirement. The orifice 66 may, but need not, be formed at an angle to a proximal surface 70a of the nozzle 64. The angle may be about 0 degrees (e.g., the orifice is substantially perpendicular to the proximal surface 70a), about 10 degrees, about 20 degrees, about 30 degrees, about 40 degrees, about 50 degrees, about 60 degrees, or some other angle. The orifice 66 shown in FIGS. 5A and 5B comprises a proximal portion 68a that can be substantially cylindrical with a length $L_1$ and a diameter $D_1$. The orifice 66 can comprise a distal portion 68b that can be substantially conical with a cone angle α and can have a length $L_2$ and a diameter $D_2$. As schematically illustrated in FIG. 5B, the cone angle α can be about 180 degrees, so that the distal portion 68b is substantially cylindrical. The diameter $D_2$ can, but need not be, different from the diameter $D_1$. For example, in various embodiments, $D_2$ can be approximately the same as $D_1$, $D_2$ can be larger than $D_1$, or $D_2$ can be smaller than $D_1$. The length $L_2$ can, but need not be, different from the length $L_1$. For example, in various embodiments, $L_2$ can be approximately the same as $L_1$, $L_2$ can be larger than $L_1$, or $L_2$ can be smaller than $L_1$. The orifice geometry schematically illustrated in FIGS. 5A and 5B may cause a relatively abrupt change in velocity of the liquid flowing through the orifice 66.

For length-to-diameter ratios $L_1/D_1$ in a range from about 0 to about 0.7, the flow may be constricted, may not reattach to the walls of the orifice, and may form a CC-Jet with a relatively long break-up length. For length-to-diameter ratios $L_1/D_1$ in a range from about 0.7 to about 4, cavitation may be induced. Initially, the flow out of the nozzle 64 may reattach to the walls of the orifice 66, and the fluid stream may not be a CC jet. For sufficiently high pressures (near the inlet 74 to the nozzle 64), cavitation may occur near the inlet 74. The cavitation region can grow and may form an air entrainment region sufficiently large to induce air from downstream to flow up to the nozzle's outlet 76 and separate liquid from the walls of the orifice 66, which may help create a CC jet. In other embodiments, length-to-diameter ratios $L_1/D_1$ above 4 can be used.

A possible advantage of using length-to-diameter ratios $L_1/D_1$ in the range from about 0 to about 0.7 is that cavitation, which may cause damage to the nozzle, may not occur. A possible disadvantage is that a sufficiently hard material able to withstand relatively high pressure may be used for the nozzle 64. A possible advantage of using length-to-diameter ratios $L_1/D_1$ in the range from about 0.7 to about 4 is that the larger $L_1/D_1$ ratio allows the nozzle's geometry to be adapted for a wider range of materials. A possible disadvantage of higher $L_1/D_1$ ratios is that cavitation may cause damage to the nozzle 64 and lead to a shorter working life for the nozzle.

It is believed, although not required, that for $L_1/D_1$ ratios at least in the range from about 0 to about 4, the nozzle design may be relatively insensitive to the cone angle α. Accordingly, cone angles near about 0 degrees can be used (e.g., the orifice 64 is approximately a cylinder over the length $L_1$ and $L_2$). In this case, the orifice 66 may be thought of as comprising just the proximal portion 68a and not the distal portion 68b. In other embodiments, only the distal portion 68b is used, and the orifice 66 is substantially conical. Many possible configurations of the orifice 66 can be used, and the examples in FIGS. 5A and 5B are intended to be illustrative and not to be limiting.

For example, as schematically illustrated in FIG. 5B, cone angles of about 180 degrees can be used. In this example, both the proximal portion 68a and the distal portion 68b are substantially cylindrical, with the diameter $D_2$ of the distal portion 68b larger than the diameter $D_1$ of the proximal portion 68a. In other embodiments, the diameter $D_2$ of the distal portion 68b may be smaller than the diameter $D_1$ of the proximal portion 68a. Shaping the proximal portion 68a or the distal portion 68b substantially as cylinders may advantageously make manufacturing the orifice simpler. In other embodiments, cone angles in a range from about 0 degrees to about 20 degrees, about 20 degrees to about 45 degrees, about 45 degrees to about 90 degrees, about 90 degrees to about 120 degrees, or some other range can be used.

In various embodiments of the nozzle 64, the orifice 66 may have a diameter $D_1$ at the inlet 74 or a diameter $D_2$ at the outlet 76 that may be in a range from about 5 microns to about 1000 microns. Other diameter ranges are possible. In various embodiments, one or both of the diameters $D_1$ or $D_2$ may be in a range from about 10 microns to about 100 microns, a range from about 100 microns to about 500 microns, or range from about 500 microns to about 1000 microns. In various other embodiments, one or both of the orifice diameters $D_1$ or $D_2$ may be in a range of about 40-80 microns, a range of about 45-70 microns, or a range of about 45-65 microns. In one embodiment, the orifice diameter $D_1$ is about 60 microns. The ratio of axial length $L_1$ to diameter $D_1$, the ratio of axial length $L_2$ to diameter $D2$, or the ratio of total axial length $L_1+L_2$ to diameter $D_1$, $D_2$, or average diameter $(D_1+D_2)/2$ may, in various embodiments, be about 50:1, about 20:1, about 10:1, about 5:1, about 1:1, or less. In one embodiment, the axial length $L_1$ is about 500 microns. In some cases, the axial length $L_2$ (or the ratio $L_2/D_2$) can be selected so that the flow through the orifice 66 does not reattach to surface 70c. The axial length $L_2$, the diameter $D_2$, or other parameters shown in FIGS. 5A and 5B may be selected so that the nozzle 64 has sufficient structural rigidity to withstand load from pressurized fluid.

With reference to the example nozzle 64 schematically illustrated in FIG. 5A, the curvature of corner or edge 69 is denoted by r, and the surface roughness of surfaces 70a, 70b, and 70c is denoted by Ra. Relatively abrupt geometry changes in the nozzle 64 may induce a relatively large velocity change, which may lead to a relatively constricted jet. For example, the ratio of surface roughness Ra to orifice diameter $D_1$, $Ra/D_1$, for some or all of the surfaces 70a-70c may be less than about 0.01, less than about 0.005, or less than about 0.001 in various embodiments. The ratio of corner curvature radius r to orifice diameter $D_1$, $r/D_1$, may be less than about 0.1, less than about 0.05, less than about 0.04, less than about 0.02, or less than about 0.01 in various embodiments. The surface roughness Ra of the surfaces 70a, 70b, or 70c can have a root-mean-square (rms) surface roughness less than about 10 microns, less than about 1 micron, or less than about 0.1 microns.

In certain embodiments, the nozzle 64 (or surface portions adjacent the liquid) can be formed from a hydrophobic material. In certain such embodiments, the contact angle (e.g., the angle formed between a solid surface and a liquid) of the hydrophobic material may be smaller than about π/2 radians. In some implementations, the nozzle 64 may comprise stainless steel or a plastic such as, e.g., acrylic. Other materials may be used such as, e.g., aluminum, copper, or polycarbonate, but in some cases, nozzles formed from such materials may not produce a substantially constricted jet.

Figure 6:
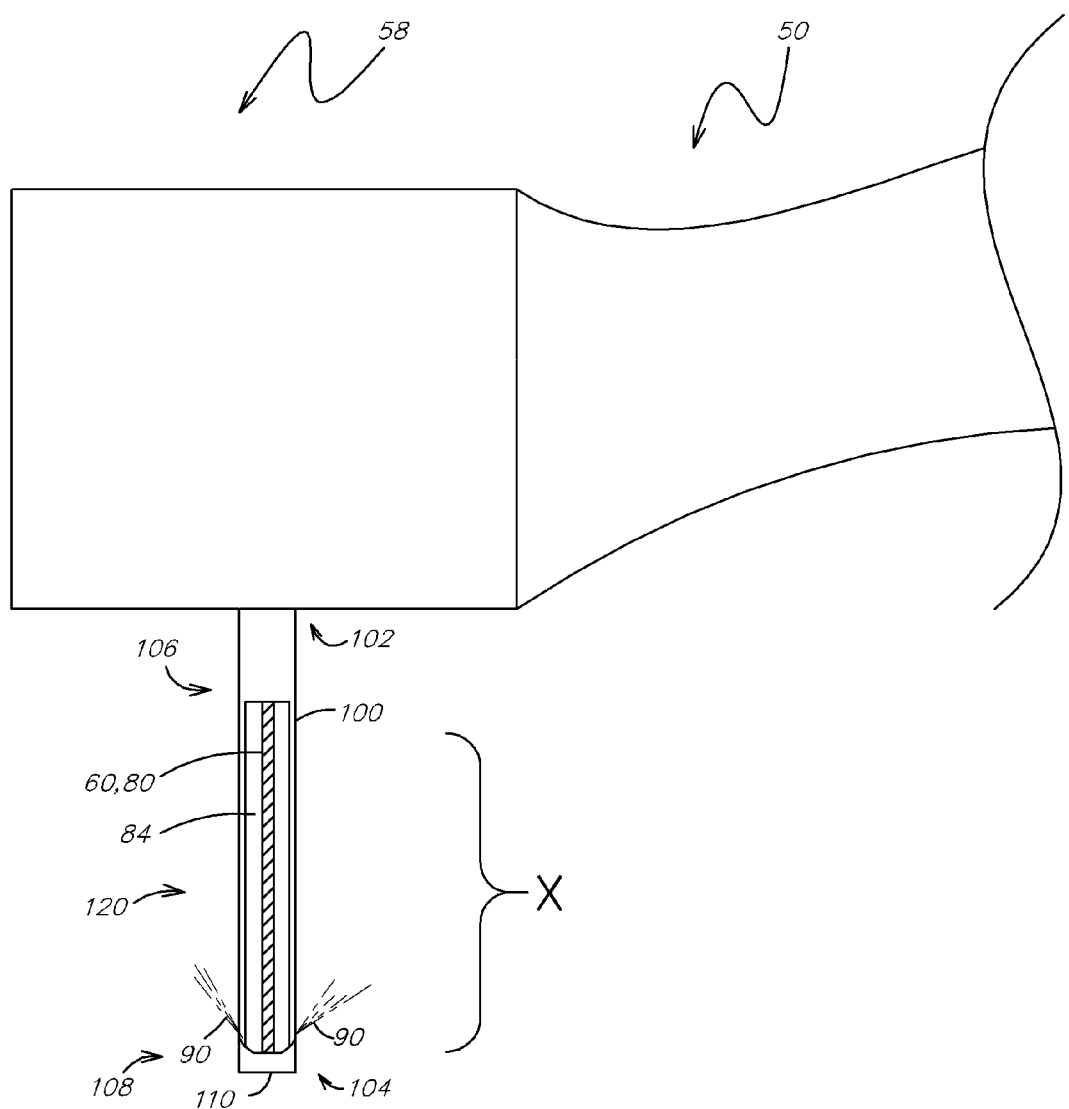
FIG. 6 is a side view schematically illustrating the distal end of an embodiment of a handpiece comprising an embodiment of a guide tube.

FIG. 6 is a side view schematically illustrating the distal end 58 of an embodiment of a handpiece 50 comprising an embodiment of a guide tube 100. FIGS. 7A-7B are side views schematically illustrating alternative embodiments of the distal ends 58 of handpieces 100 comprising embodiments of guide tubes 100. In the illustrated embodiments, the guide tube 100 comprises a substantially straight, elongated, cylindrical tube. In other embodiments, the guide tube 100 may have a different shape (e.g., curved) or a different cross-section (see, e.g., FIGS. 10A-10F below). In some embodiments, the guide tube 100 comprises a plurality of tubes that may at least partially disposed in, on, or around each other (e.g., to form a "telescoping" configuration). For example, the guide tube 100 may comprise at least a first tube and a second tube configured such that the proximal end of the second tube is disposed in the distal end of the first tube (see, e.g., an example shown in FIG. 22A).

With reference to FIG. 6, the guide tube 100 has a proximal end 102 that can be attached or disposed adjacent the distal end 58 of the handpiece 50 and a distal end 104 that, during treatment, can be disposed in, near, or on a portion of the tooth 10 under treatment. For example, the distal end 104 of the guide tube 100 can be disposed in a cavity in the tooth 10. The cavity may include natural or artificial spaces, openings, or chambers in the tooth such as, e.g., the pulp chamber 28, a canal space 30, an opening drilled or formed in the tooth by a dental practitioner, etc. The guide tube 100 has a channel 84 that permits propagation of the liquid jet 60 along at least a portion of the length of the guide tube 100. For example, the liquid jet 60 may propagate along the longitudinal jet axis 80. In the embodiments schematically depicted in FIGS. 6 and 7A-7B, the longitudinal jet axis 80 is substantially collinear with the longitudinal axis of the channel 84 and the guide tube 100. In other embodiments, the longitudinal jet axis 80 may be offset from the longitudinal axis of the channel 84 and/or the guide tube 100, for example, by offsetting the orifice 66 of the nozzle 64 from relative to the axes of the channel 84 and/or guide tube 100.

In various embodiments of the guide tube 100, the cross-section of the channel 84 can be substantially closed (e.g., a lumen) (see, e.g., FIGS. 10A-10F described below). In other embodiments, the cross-section of the channel 84 can be partially open at least along a portion of the length of the guide tube 100. For example, the cross-section of the channel 84 may have a generally C-shape or U-shape. A possible advantage of certain embodiments of guide tubes 100 comprising a substantially closed channel 84 is that the jet is protected from disruption by elements outside the channel 84 as the jet propagates through the guide tube 100. Also, use of a substantially closed channel 84 may reduce the likelihood of air entering the pulp chamber 26 during treatment.

The proximal end 102 of the guide tube 100 can be attached to the distal end 58 of the dental handpiece 50. The liquid jet 60 (which may be a CC jet) can propagate from the handpiece 50 along the jet axis 80, which can pass through the channel 84 of the guide tube 100. It is advantageous, in some embodiments, if the guide tube 100 is positioned and/or oriented on the handpiece 50 so that the jet axis 80 is aligned substantially parallel to the longitudinal axis of the channel 84 of the guide tube 100 in order that the liquid jet 60 propagates along the channel and does not impact a wall of the guide tube (except as further described below). In some embodiments, the jet axis 80 may be offset from the longitudinal axis of the channel 84 or the guide tube 100.

Embodiments of the guide tube 100 can be sized or shaped such that the distal end 104 can be positioned through an endodontic access opening formed in the tooth 10, for example, on an occlusal surface, a buccal surface, or a lingual surface. For example, the distal end 104 of the guide tube may be sized or shaped so that the distal end 104 can be positioned in the pulp cavity 26 of the tooth 10, e.g., near the pulpal floor, near openings to the canal space 30, or inside the canal openings. The size of the distal end 104 of the guide tube 100 can be selected so that the distal end 104 fits through the access opening of the tooth 10. In some embodiments, the width of the guide tube 100 can be approximately the width of a Gates-Glidden drill, for example, a size 4 drill. In some embodiments, the guide tube 100 can be sized similarly to gauge 18, 19, 20, or 21 hypodermic tubes. The width of the guide tube 100 may be in a range from about 0.1 mm to about 5 mm, in a range from about 0.5 mm to about 1.5 mm, or some other range. The length of the guide tube 100 can be selected so that the distal end 104 of the guide tube 100 can be disposed at a desired location in the mouth. For example, the length of the guide tube 100 between the proximal end 102 and the distal end 104 may be in a range from about 1 mm to about 50 mm, from about 10 mm to about 25 mm, or in some other range. In some embodiments, the length is about 18 mm, which may allow the distal end 104 of the guide tube 100 to reach the vicinity of the pulpal floor in a wide range of teeth. For teeth that may not have a pulpal chamber or a pulpal floor (e.g., anterior teeth), the distal end 104 of the guide tube 100 can be inserted into the canal space of the tooth 10.

As schematically illustrated in FIGS. 6 and 7A-7B, certain embodiments of the guide tube 100 can comprise an impingement member 110 (which also may be referred to herein as a deflector). The jet 60 can propagate along the channel 84 and impinge upon the impingement member 110, whereby at least a portion of the jet 60 can be slowed, disrupted or deflected, which can produce a spray 90 of liquid. The spray 90 may comprise droplets, beads, mist, jets, or beams of liquid in various implementations. Embodiments of the guide tube 100 which include an impingement member 110 may reduce or prevent possible damage that may be caused by the jet during certain dental treatments. For example, use of the impingement member 110 may reduce the likelihood that the jet may undesirably cut tissue or propagate into the root canal spaces 30 (which may undesirably pressurize the canal spaces in some cases). The design of the impingement member 110 (further described below) may also enable a degree of control over the fluid circulation or pressure waves that can occur in the pulp cavity 26 during treatment.

The impingement member 110 may be disposed in a cavity in the tooth 10. In some methods, the impingement member 110 is disposed in fluid in the tooth 10, and the liquid jet 60 impacts an impingement surface of the impingement member 110 while the impingement member 110 is disposed in the cavity. The liquid jet 60 may be generated in air or fluid, and in some cases, a portion of the liquid jet 60 passes through at least some (and possibly a substantial portion) of fluid in the cavity in the tooth 10 before impacting the impingement member 110. In some cases, the fluid in the tooth cavity may be relatively static; in other cases, the fluid in the tooth cavity may circulate, be turbulent, or have fluid velocities that are less than (or substantially less than) the speed of the high-velocity liquid jet.

In some implementations, the impingement member 110 is not used, and the jet 60 can exit the guide tube 100 without substantial interference from portions of the guide tube 100. In some such implementations, after exiting the guide tube 100, the jet 60 may be directed toward a dentinal surface, where the jet may impact or impinge upon the dentinal surface to provide acoustic energy to the tooth, to superficially clean the tooth, and so forth.

The guide tube 100 can include an opening 120 that permits the spray 90 to leave the distal end 104 of the guide tube 100. In some embodiments, multiple openings 120 can be used (see, e.g., FIGS. 18-20E), for example, two, three, four, five, six, or more openings. The opening 120 can have a proximal end 106 and a distal end 108. The distal end 108 of the opening 120 can be disposed near the distal end 104 of the guide tube 100. The opening 120 can expose the liquid jet 60 (and/or the spray 90) to the surrounding environment, which may include air, liquid, organic material, etc. For example, in some treatment methods, when the distal end 104 of the guide tube 100 is inserted into the pulp cavity 120, the opening 120 permits the material or fluid inside the pulp cavity 26 to interact with the jet 60 or spray 90. A hydroacoustic field (e.g., pressure waves, acoustic energy, etc.) may be established in the tooth 10 (e.g., in the pulp cavity 26, the canal spaces 30, etc.) by the impingement of the jet 60 on the impingement member 110, interaction of the fluid or material in the tooth 10 with the jet 60 or they spray 90, fluid circulation or agitation generated in the pulp cavity 26, or by a combination of these factors (or other factors). The hydroacoustic field may include acoustic power over a relatively broad range of acoustic frequencies (e.g., from about a few kHz to several hundred kHz or higher). The hydroacoustic field in the tooth may influence, cause, or increase the strength of effects including, e.g., acoustic cavitation (e.g., bubble formation and collapse, microjet formation), fluid agitation, fluid circulation, sonoporation, sonochemistry, and so forth. It is believed, although not required, that the hydroacoustic field, some or all of the foregoing effects, or a combination thereof may act to disrupt or detach organic material in the tooth, which may effectively clean the pulp cavity 26 and/or the canal spaces 30.

The length of the opening 120 between the proximal end 106 and the distal end 108 is referred to as X (see, e.g., FIG. 6). In various embodiments, the length X may be in a range from about 0.1 mm to approximately the overall length of the guide tube 100. For example, FIGS. 6 and 7A-7B show three guide tube embodiments having different opening lengths. In some embodiments, the length X is in a range from about 1 mm to about 10 mm. In some cases, the length X is selected so that the opening 120 remains submersed by fluid or material in the pulp cavity 26 of the tooth 10 during treatment. A length X of about 3 mm can be used for a wide variety of teeth. In some embodiments, the length X is a fraction of the overall length of the guide tube 100. The fraction can be about 0.1, about 0.25, about 0.5, about 0.75, about 0.9, or a different value. In some embodiments, the length X is a multiple of the width of the guide tube 100 or the channel 84. The multiple can be about 0.5, about 1.0, about 2.0, about 4.0, about 8.0, or a different value. The multiple can be in a range from about 0.5 to about 2.0, about 2.0 to about 4.0, about 4.0 to about 8.0, or more. In other embodiments, the length X is a multiple of the width of the jet, e.g., 5 times, 10 times, 50 times, or 100 times the width of the jet. The multiple can be in a range from about 5 to about 50, about 50 to about 200, about 200 to about 1000, or more. In some implementations, the length X of the opening 120 can be selected (at least in part) such that the hydroacoustic field generated in a tooth has desired properties including, e.g., desired acoustic power in the tooth at one or more acoustic frequencies.

Figures 8A, 8B:
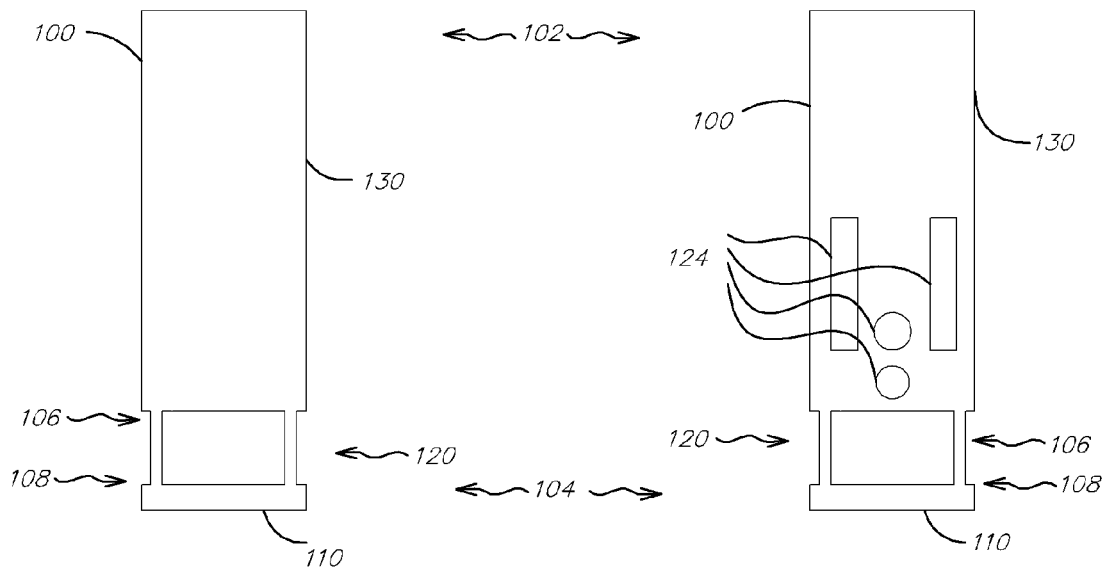
FIGS. 8A-8C are side views that schematically illustrate additional embodiments of guide tubes.
Figure 8C:
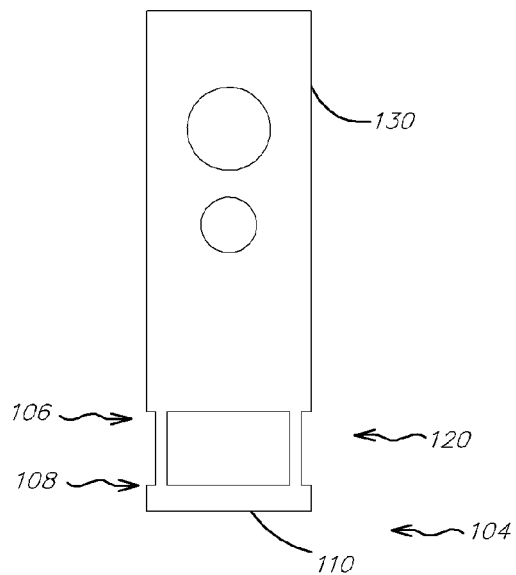

FIGS. 8A-8C are side views that schematically illustrate additional embodiments of guide tubes. The embodiments of the guide tubes 100 shown in FIGS. 8A-8C comprise a body 130 that extends from the proximal end 102 of the guide tube 100 to the proximal end 106 of the opening 120. In the embodiment schematically depicted in FIG. 8A, the body 130 does not include any holes and the wall or walls of the body 130 are substantially solid. In the embodiments schematically depicted in FIGS. 8B and 8C, the body 130 includes one or more holes 124. The holes 124 can have any desired shape, arrangement, or placement along the body 130. During operation of the jet 60, the relatively high speed of the jet 60 may tend to draw air into the channel 84 of the guide tube 100 through any holes 124 (if present and if not submersed in surrounding fluid). The air can travel alongside the jet 60 toward the distal end 104 of the guide tube 100. In some treatment methods, the drawn air may enter the pulp cavity 26, which may, in some cases, may draw air into the canal spaces 30. Also, the drawn air may, in some cases, diminish the acoustic power or fluid circulation provided by the jet 60. Therefore, a possible advantage of the guide tube 100 schematically depicted in FIG. 8A is that the lack of holes on the body 130 can inhibit or prevent air from being drawn into the guide tube during treatment. In some embodiments, holes 124 are used on the guide tube, but the holes 124 are disposed near the proximal end 106 of the opening 120 so that during treatment the holes remain submersed in fluid present in the pulp cavity 26. In other embodiments, holes 124 that may be exposed to air are used on the guide tube 100, and the size of such holes 124 are sufficiently small not to substantially draw air into the guide tube 100 during treatment with the liquid jet 60. For example, such holes 124 may have sizes less than about 300 µm, less than about 700 µm, less than about 1000 µm, or some other size.

FIGS. 4 and 4A schematically illustrate an embodiment of the handpiece 50 in which the nozzle 64 is disposed in a nozzle mount 62 near the distal end 58 of the handpiece 50. In other embodiments, the nozzle 64 can be located in other locations in the handpiece 50 or the guide tube 50. FIGS. 9A-9D are cross-section views that schematically illustrate various embodiments of handpieces 50, guide tubes 100, and locations of nozzles 64. In FIGS. 9A-9D, the handpiece 50 comprises a conduit 57 having a passageway 54 through which pressurized liquid delivered by the system 38 can flow. In the embodiments of the handpiece 50 shown in FIGS. 9A, 9B, and 9D, an external portion 57a of the conduit 57 extends away from the distal end 58 of the handpiece. The guide tube 100 comprises the external portion 57a of the conduit 57 and (optionally) an end portion 57b. In the embodiments shown in FIGS. 9A, 9B, and 9D, the end portion 57b comprises the impingement member 100 and the opening 120. In the embodiments shown in FIGS. 9A, 9B, and 9D, the nozzle 64 is disposed at the distal end of the external conduit 57a. In the example embodiments shown in FIGS. 9A and 9B, the overall length of the guide tube 100 is about the same, with the external conduit 57a being longer (shorter) and the end portion 57b being shorter (longer) in FIGS. 9A and 9B, respectively. In other embodiments, the relative lengths of the external conduit 57a (if any) and the end portion 57b (if any) may be selected as desired. For example, in some cases, the external conduit 57a may be more rigid than the end portion 57b (e.g., because the conduit may have thicker walls), and if increased rigidity is desired, the length of the external conduit 57a may be longer than the length of the end portion 57b (if any). As another example, in other cases it may be easier to form the opening 120 in the end portion 57b (e.g., because the end portion may have thinner walls), and in some such cases, the end portion 57b may be made relatively longer. In some embodiments, the nozzle 64 can be formed integrally with the conduit 57 or 57a. In some such embodiments, the orifice 66 may be formed at a distal end surface of the conduit 57 or 57a (e.g., via laser cutting or EDM).

Figure 9A:
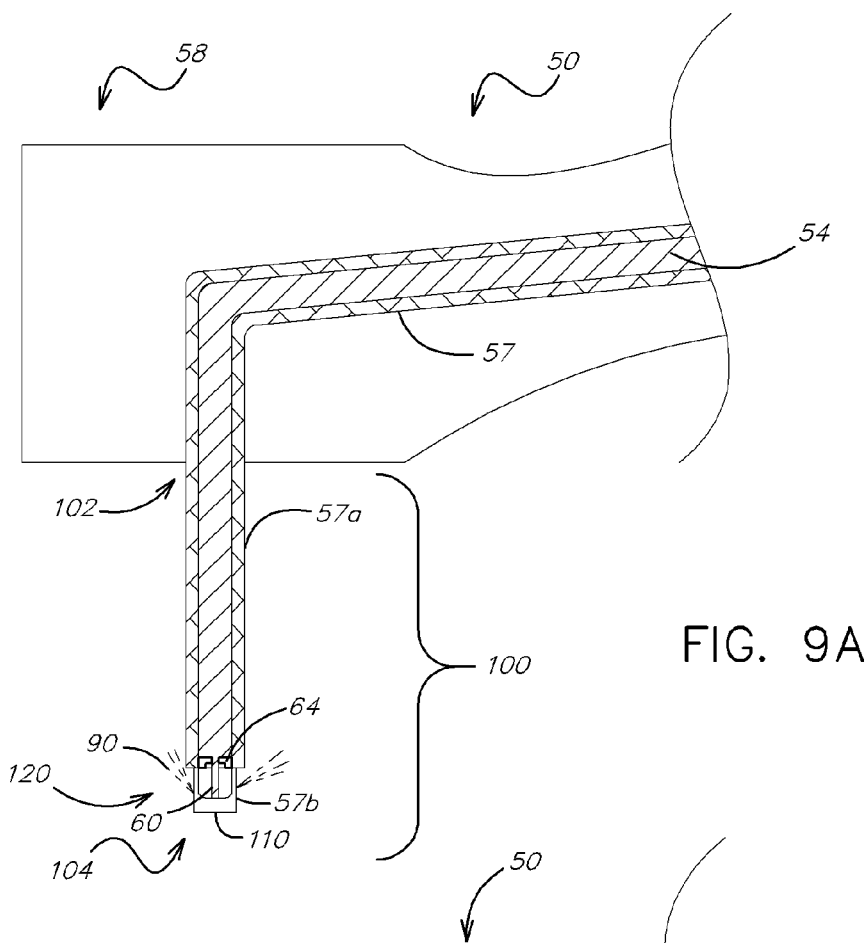
FIGS. 9A-9D are cross-section views that schematically illustrate various embodiments of handpieces, guide tubes, and nozzle locations.
Figure 9B:
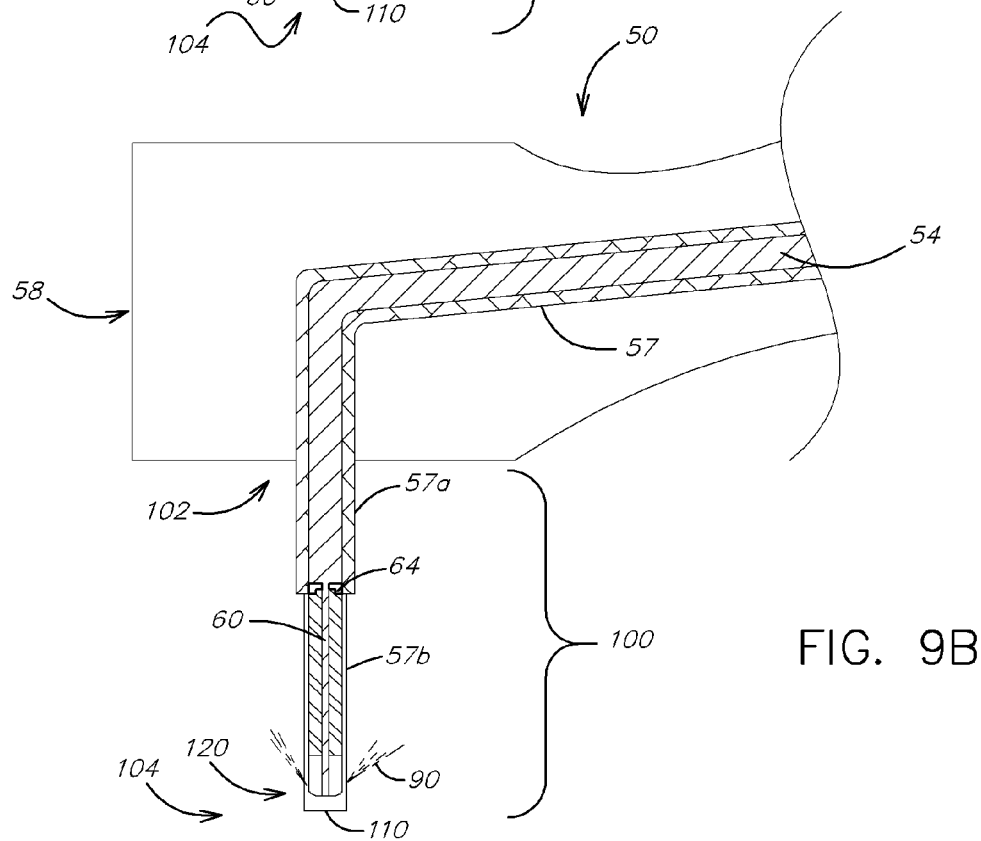
Figure 9C:
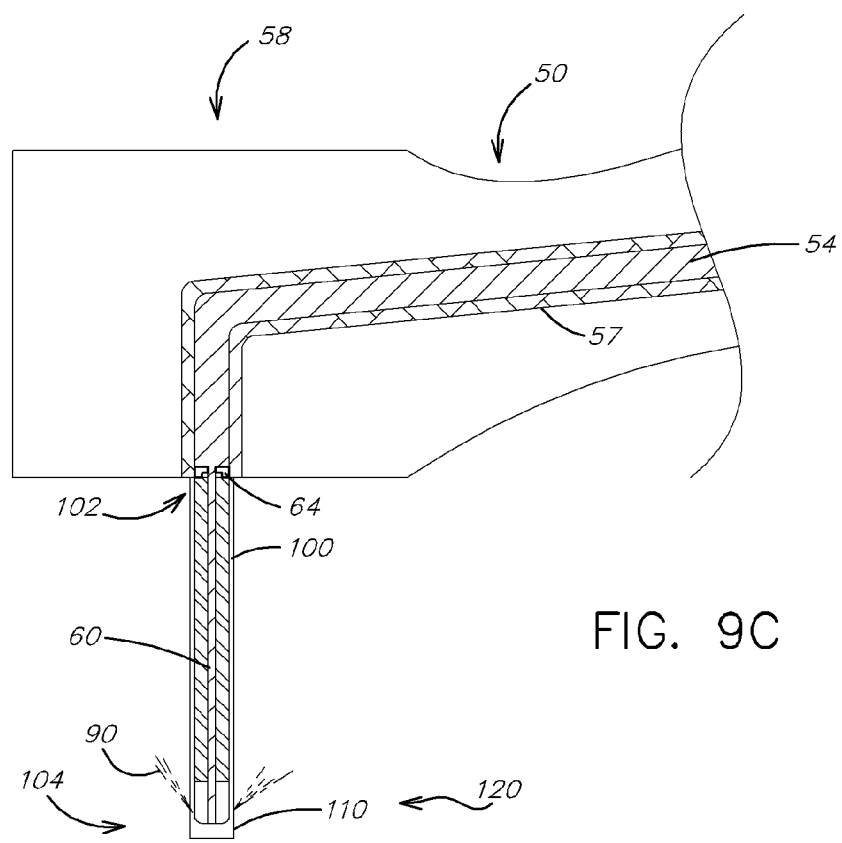
Figure 9D:
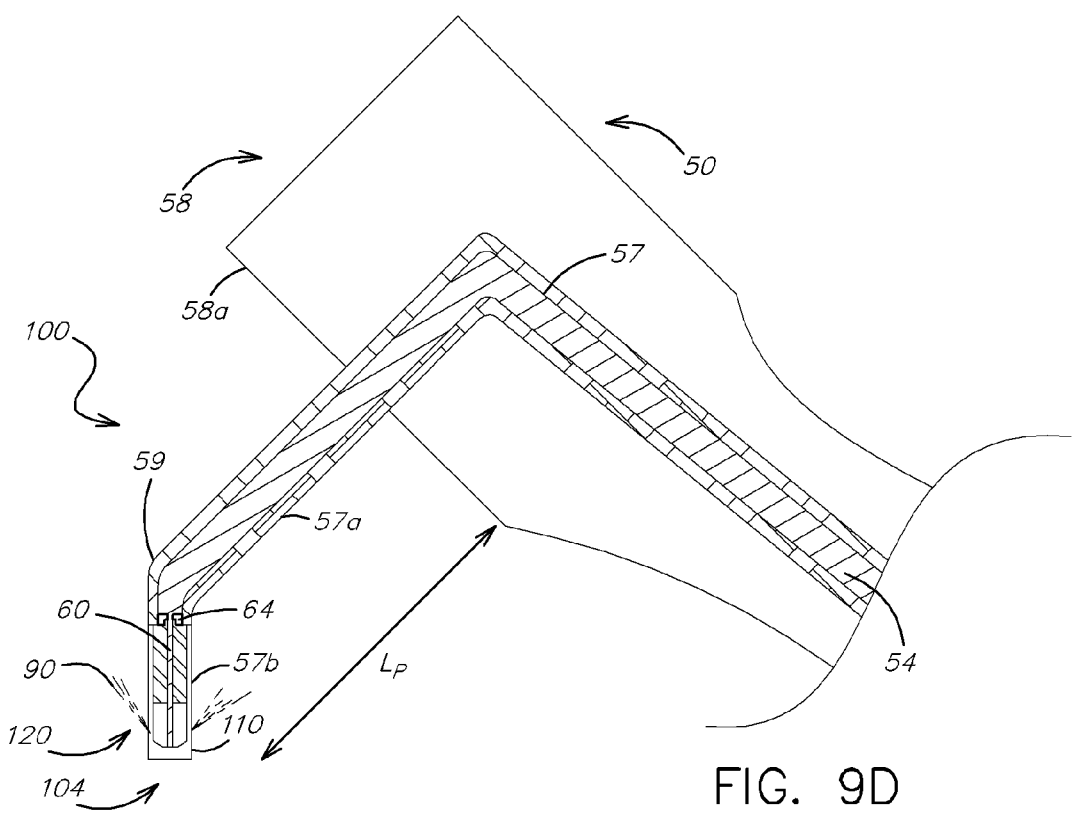

FIG. 9D shows an embodiment of the handpiece 50 in which the guide tube 100 comprises a bend 59. In this illustrative example, the bend 59 is located on the external conduit 57a. In other embodiments, the bend (or additional bends) may be located elsewhere along the guide tube 100, e.g., along the end portion 57b (if used). Guide tubes comprising bends may assist a dental practitioner in disposing the distal end 104 of the guide tube 100 in a desired location in the patient's mouth. A guide tube 100 comprising one or more bends may have a shorter profile length $L_P$ measured perpendicularly from a distal surface 58a of the handpiece to the distal end 104 of the guide tube 100 than a straight guide tube 100 having the same overall length (measured along the guide tube). The shorter profile length of some guide tube embodiments may allow the guide tube to be more easily positioned in the mouth or to reach pulpal cavities. Certain teeth may lack a pulpal floor (e.g., anterior teeth) or a crown. For such teeth, a relatively short profile guide tube 100 may make delivering the jet 60 or spray 90 to the desired region in the tooth easier.

FIG. 9C shows an embodiment of the handpiece 50 in which an external conduit 57a is not used. In this embodiment, the proximal end 102 of the guide tube 100 is disposed at the bottom 58a of the distal end 58 of the handpiece 50, and the nozzle 64 is disposed near the proximal end 102 of the guide tube 100. In other embodiments, the nozzle 64 is disposed near the distal end of the guide tube 100 (e.g., near the proximal end 106 of the opening 120).

Therefore, in various embodiments, the nozzle 64 can be disposed at a position upstream of the guide tube 100 (e.g., in the conduit 57 inside the handpiece 50), at a position at or near the proximal end 102 of the guide tube 100, at a position inside the guide tube 100 between the proximal end 102 of the guide tube 100 and the proximal end 106 of the opening 120, or at a position at or near the proximal end 106 of the opening 120. In some embodiments, guide tube 100 comprises a proximal portion and a distal portion. The nozzle 64 can be disposed in the distal portion of the guide tube 100 such that the distal portion extends distally beyond the nozzle 64. The distal portion extending distally beyond the nozzle 64 may include the impingement member 110. In some such embodiments, the proximal portion comprises a proximal half of the guide tube 100, and the distal portion comprises a distal half of the guide tube 100.

Figure 10A:
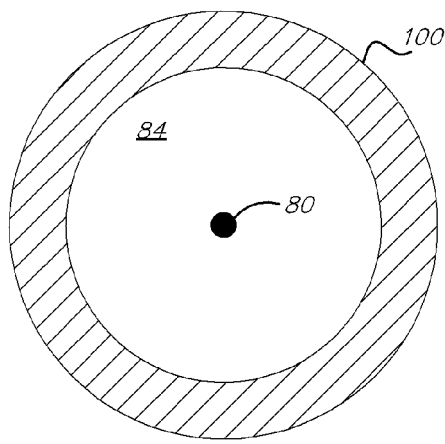
FIGS. 10A-10F are cross-section views schematically illustrating embodiments of guide tubes.
Figure 10B:
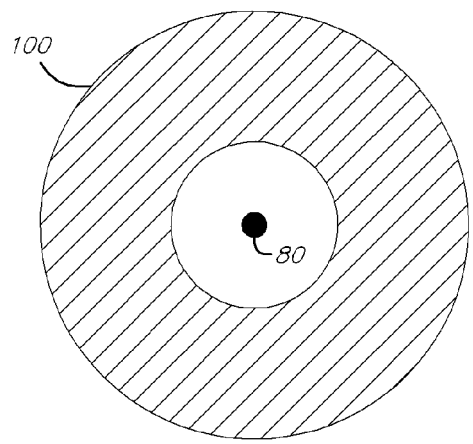
Figure 10C:
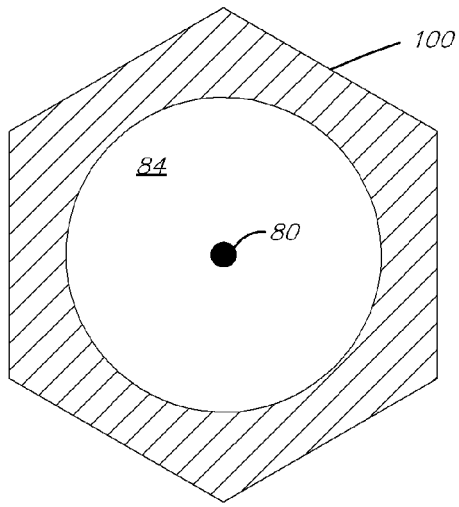
Figure 10D:
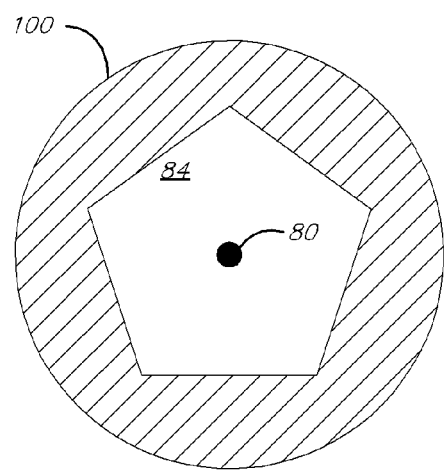
Figure 10E:
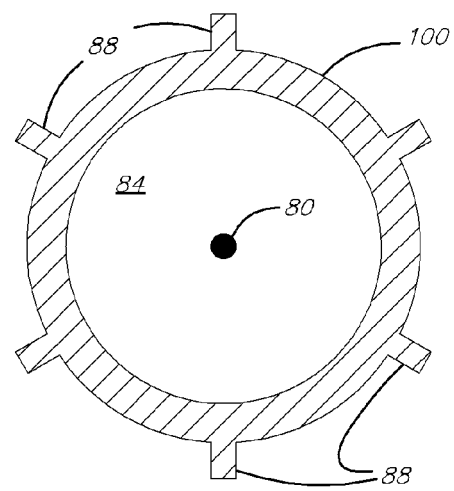
Figure 10F:
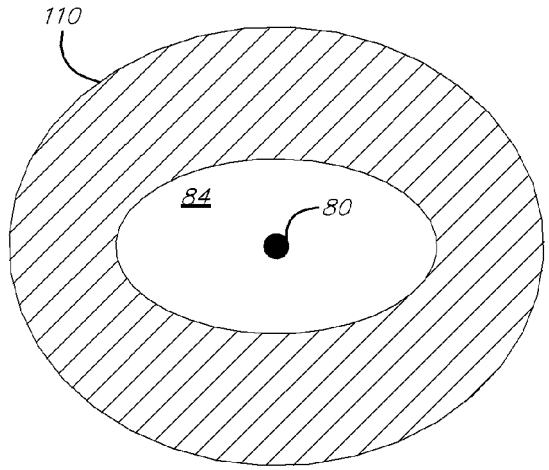

FIGS. 10A-10F are cross-section views schematically illustrating various embodiments of the guide tubes 100. The cross-section of the channel 84 and/or the guide tube 100 may be substantially circular (see, e.g., FIGS. 10A, 10B, 10D), oval (see, e.g., FIG. 10F), rectangular, polygonal (e.g., hexagonal as shown in FIG. 10C for the guide tube and pentagonal as shown in FIG. 10D for the channel), or some other shape. The cross-sectional shape and/or size of the guide tube 100 and/or the channel 84 can vary along the longitudinal axis of the guide tube 100. The cross-sectional shape of the channel 84 can be the same as or different from the cross-sectional shape of the guide tube 100 (see, e.g., FIGS. 10C and 10D). In certain embodiments, the cross-sectional shapes of the channel and the guide tube are substantially circular, and the channel is substantially concentric with the guide tube (see, e.g., FIGS. 10A and 10B). The guide tube 100 may comprise one or more extensions 88, which may run longitudinally along the guide tube 100, which may increase the strength of the tube (see, e.g., FIG. 10E).

In some embodiments, the cross-section of the guide tube 100 is larger at the proximal end 102 than at the distal end 104, which may increase the rigidity of the guide tube 100. In various embodiments, the cross-section of the channel 84 may change along the longitudinal axis 80 of the guide tube (e.g., narrowing toward the distal end 104) or the cross-section of the channel may be substantially constant. The longitudinal axis of the channel 84 can, but need not, be substantially collinear with the longitudinal axis 80 of the guide tube 100. In some embodiments, the orifice 66 is aligned with the longitudinal axis of the channel or the guide tube. The surface of the channel 84 may be substantially smooth, which beneficially may reduce the likelihood of turbulent air flow interfering with or disrupting the jet. In some embodiments, the surface of the channel 84 can be contoured, curved, spiraled, or twisted.

Figure 11A:
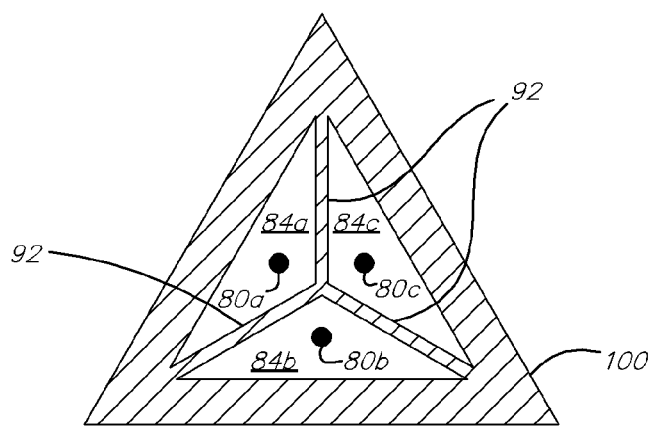
FIGS. 11A-11D are cross-section views schematically illustrating additional embodiments of guide tubes.
Figure 11B:
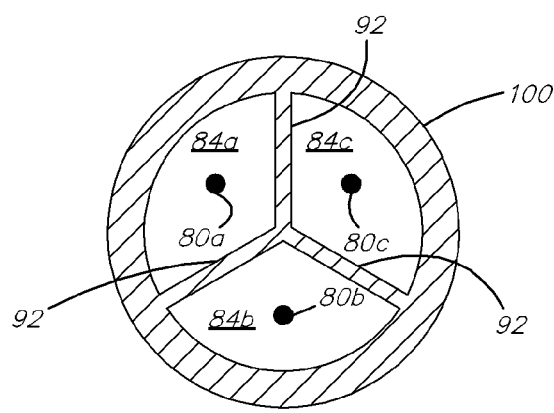
Figure 11C:
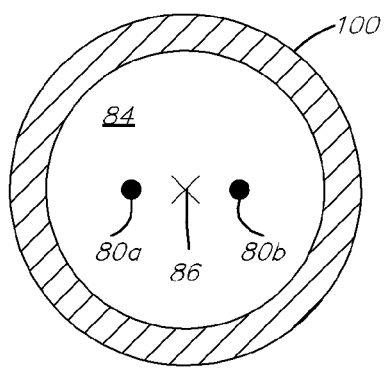

FIGS. 11A-11C are cross-section views schematically illustrating embodiments of guide tubes 100 capable of propagating multiple jets. In the embodiments shown in FIGS. 11A and 11B, the guide tubes 100 comprise multiple channels. For example, FIG. 11A shows an embodiment of the guide tube 100 having three channels 84a-84c. Each of the three channels 84a-84c is capable of propagating a jet along the corresponding longitudinal jet axes 80a-80c. FIG. 11B shows an embodiment of the guide tube 100 having four channels 84a-84d. Each of the four channels 84a-84d is capable of propagating a jet along the corresponding longitudinal jet axes 80a-80d. In other embodiments, a different number of channels may be used such as, e.g., two channels, five channels, or more. The guide tubes 100 can have structural elements 92 (e.g., baffles) that separate the channels, for example, as shown in FIGS. 11A and 11B. The structural elements 92, if used, may extend along substantially all or only a portion of the length of the guide tube 100. In some embodiments, the structural elements extend from the proximal end 102 of the guide tube 100 to the upper portion of a window in the guide tube (described below).

FIG. 11C schematically illustrates an embodiment of the guide tube 100 having a single channel 84 through which multiple jets (e.g., two jets in this embodiment) can propagate along longitudinal jet axes 80a and 80b. In other embodiments, the guide tube can be configured so that three, four, or more jets can propagate through the channel 84. In the illustrated embodiment, both jet axes 80a and 80b are offset from the longitudinal axis 86 of the channel 84. In other embodiments, one (or more) of the jet axes could be substantially aligned with the longitudinal axis 86. In some embodiments of the guide tube 100 depicted in FIG. 11C, a single nozzle 64 comprising multiple orifices 66 (e.g., two orifices for the example shown in FIG. 11C) can be used to provide the jets. In other embodiments, multiple nozzles can be used.

Figure 11D:
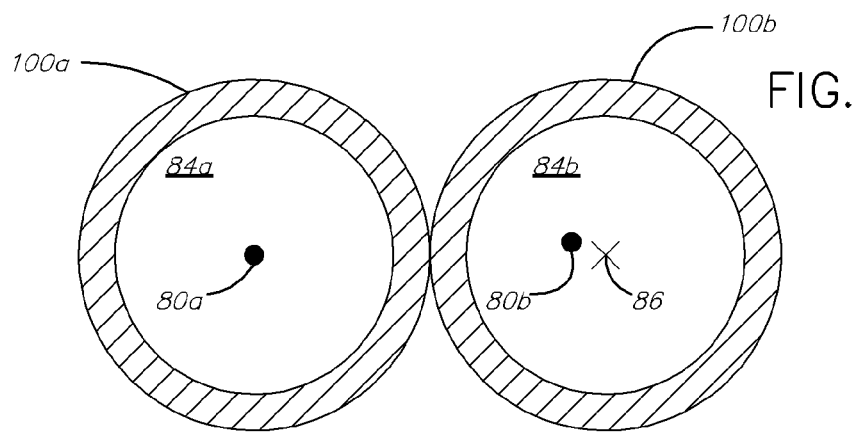

In some embodiments of the handpiece 50, multiple guide tubes 100 (e.g., two, three, four, or more) can be disposed at the distal end 58 of the handpiece 50. Each guide tube 100 can propagate one (or more) jets. FIG. 11D is a cross-section view that schematically illustrates an embodiment having two guide tubes 100a and 100b. In the guide tube 100a, the jet propagates along the jet axis 80a, which is substantially coaxial with the longitudinal channel axis and the longitudinal guide tube axis. In the guide tube 100b, the jet axis 80b is offset from the longitudinal axis 86 of the channel 84. In the illustrated embodiment, the cross-sections of the channels 84a, 84b and the guide tubes 100a, 100b are substantially circular. In other embodiments, the cross-sections of the channels or guide tubes can be different than illustrated in FIG. 11D (e.g., either or both of the guide tubes 100a, 100b could be configured similar to any of the guide tubes schematically shown in FIGS. 10A-10F or FIGS. 11A-11C). Also, in any embodiment, the cross-sections of the channels or guide tubes can be different from each other (e.g., the cross-section of the channel 84a or the guide tube 100a can be different from the cross-section of the channel 84b or the guide tube 100b). In the embodiment schematically illustrated in FIG. 11D, the guide tubes 100a, 100b are disposed next to each other and are in contact. In some embodiments, the guide tubes can be arranged in a closely-packed configuration, whereas in other embodiments, some or all of the guide tubes may be physically spaced from each other.

Figure 12A:
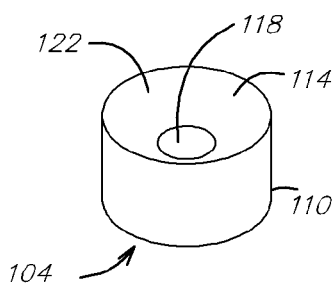
FIGS. 12A-12E include perspective views (left-hand panel) and side views (right-hand panel) schematically illustrating embodiments of the impingement member.
Figure 12A:
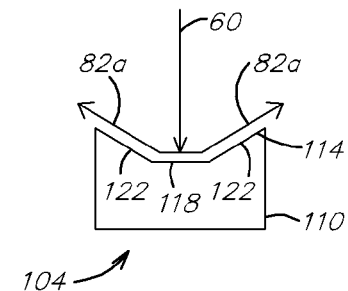
Figure 12B:
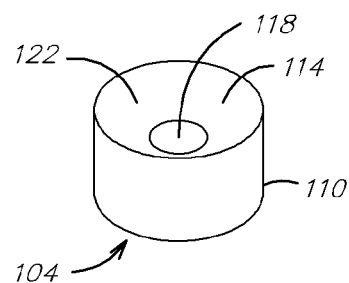
Figure 12B:
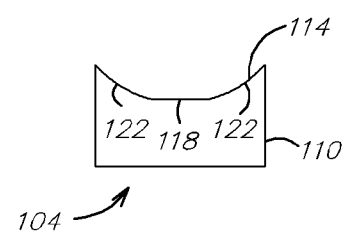
Figure 12C:
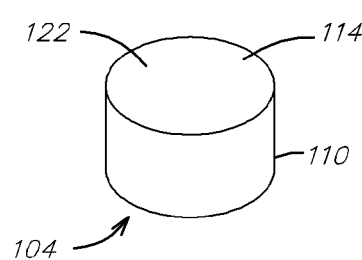
Figure 12C:
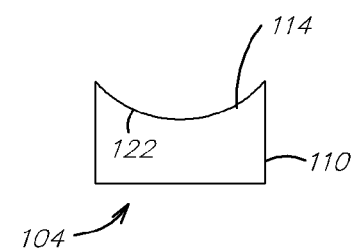
Figure 12D:
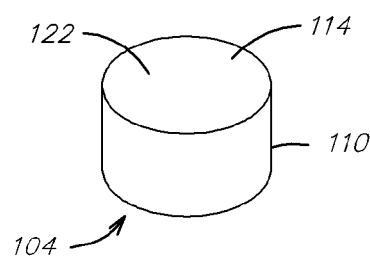
Figure 12D:
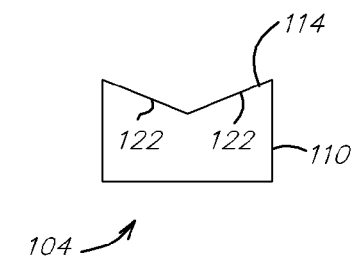
Figure 12E:
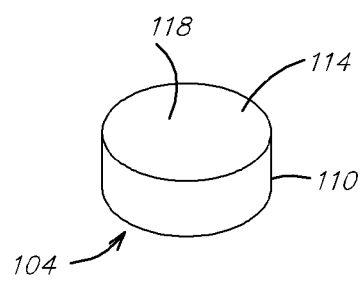
Figure 12E:
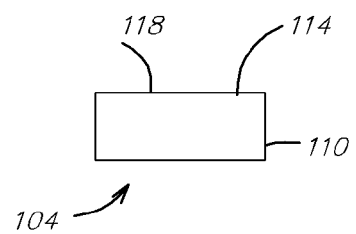
Figure 13A:
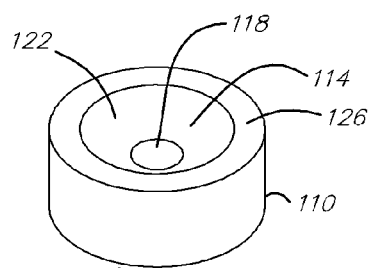
FIGS. 13A-13E include perspective views (left-hand panel) and side views (right-hand panel) schematically illustrating additional embodiments of the impingement member.
Figure 13A:
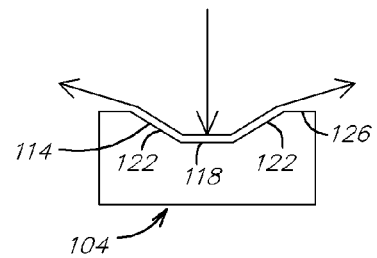
Figure 13B:
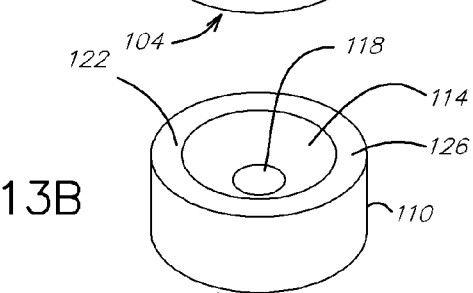
Figure 13B:
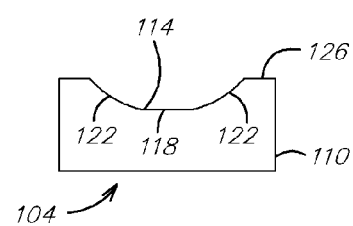
Figure 13C:
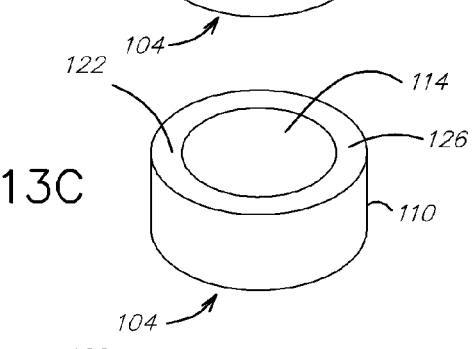
Figure 13C:
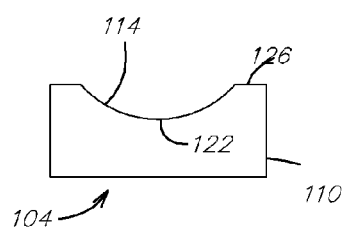
Figure 13D:
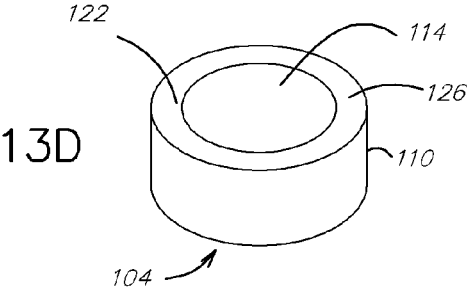
Figure 13D:
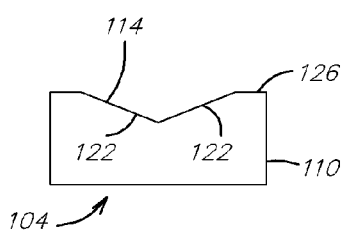

FIGS. 12A-12E and FIGS. 13A-13E include perspective views (left-hand panel) and side views (right-hand panel) schematically illustrating various embodiments of the impingement member 110, which may be used to convert the liquid jet 60 into the spray 90. The impingement member 110 has an impingement surface 114 upon which the liquid jet 60 can impinge during operation of the jet apparatus. The impingement surface 114 may, but need not, include a substantially flat section 118 that may be disposed near the center of the impingement member 110 to intercept the jet 60 (see, e.g., FIGS. 12A, 12B, 12E and FIGS. 13A, 13B, and 13E). The impingement surface 114 may, but need not, include angled or curved sections 122 that angle or curve back toward the direction of the oncoming jet 60 (e.g., away from the distal end 104 of the guide tube) and which may help direct some of the jet 60 (or the spray 90) back towards the proximal end 106 of the opening 120 (see, e.g., the spray 90 schematically shown in FIGS. 6A-6C). For example, FIG. 12A (right-hand panel) schematically shows the jet 60 impinging on the substantially flat section 118 of the impingement member 110 and liquid (e.g., jets or sprays) flowing in the directions indicated by arrows 82a. A possible advantage of re-directing the liquid back toward the proximal end 106 of the opening 120 is that there may be a reduced likelihood that pressurized liquid (e.g., jet or spray) enters the canal spaces 30. Although FIGS. 12A and 13A schematically examples of use in which the spray 90 is directed toward the proximal end 106 of the opening 120 (see, e.g., the arrows 82a, 82b), the impingement surface 114 may be configured to direct the spray away from the proximal end 106 of the opening 120. For example, in other embodiments, the impingement surfaces 114 may have shapes generally similar to the surfaces 114 shown in FIGS. 12A-12E and FIGS. 13A-13E but which bulge away from the distal end 104 and toward the proximal end 106 of the opening 120 (e.g., portions of the surfaces 114 are convex rather than concave). Some such shapes may direct the jet or spray toward the distal end 104 of the guide tube and may increase fluid circulation within the pulp chamber 28 or the canal spaces 30.

The impingement surface 114 can have a variety of shapes, some of which are depicted in the examples schematically shown in FIGS. 12A-12E and 13A-13E. The impingement surfaces 114 of the embodiments in FIGS. 13A-13E may be generally similar to the corresponding embodiments shown in FIGS. 12A-12E, respectively. The embodiments in FIGS. 13A-13E include an (optional) outer substantially flat surface 126, which may cause the re-directed liquid to flow along the directions indicated by arrows 82b due to, e.g., the Coanda effect (see, e.g., the right-hand panel of FIG. 13A).

Figure 13E:
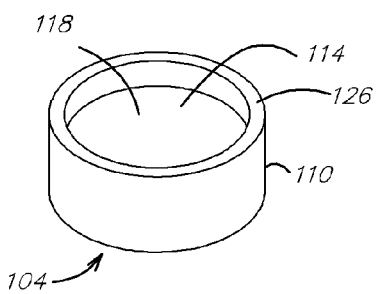
Figure 13E:
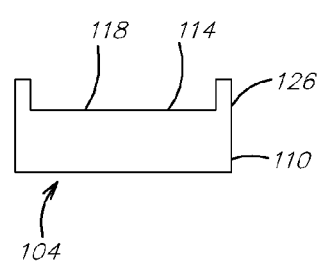

In various embodiments, the impingement surface 114 may be substantially flat (see, e.g., FIGS. 12E, 13E). The impingement surface 114 may include one or more sections 122 that angle (see, e.g., FIGS. 12A, 12D, 13A, 13E) or curve (see, e.g., FIGS. 12B, 12C, 13B, 13C) back toward the oncoming jet 60 (e.g., away from the distal end 104 of the guide tube). In some embodiments, the section 122 is formed at an angle in a range from about 5 degrees to about 45 degrees, from about 10 degrees to about 30 degrees, from about 35 to about 60 degrees, about 60 degrees to about 80 degrees, or some other range. In some embodiments, the section 122 is formed at an angle such as, e.g., about 40 degrees, about 45 degrees, about 50 degrees, or about 55 degrees. In some embodiments, the curved section 122 comprises a portion of a sphere, ovoid, ellipsoid, toroid, conic section, or other curved surface. In FIGS. 12A-12D, and 13A-13D, the impingement surface 114 is concave toward the oncoming jet, but in other embodiments, the impingement surface 114 may be convex (e.g., portions of the impingement surface 114 could extend away from, rather than toward, the distal end 104 of the guide tube). In the embodiment shown in FIG. 13E, the outer substantially flat section 126 is raised above the substantially flat section 118. The height of the raised section 126 may be selected to deflect the jet spray 90 away from the impingement surface 114 by a desired amount.

The impingement member 110 may have a cross-sectional shape or size that is the same as or different from the cross-sectional shape or size, respectively, of the channel 84 or the guide tube 100. For example, in various embodiments the width of the impingement plate 110 can be larger (or smaller) than the width of the channel 84 or the width of the guide tube 100.

Figure 14A:
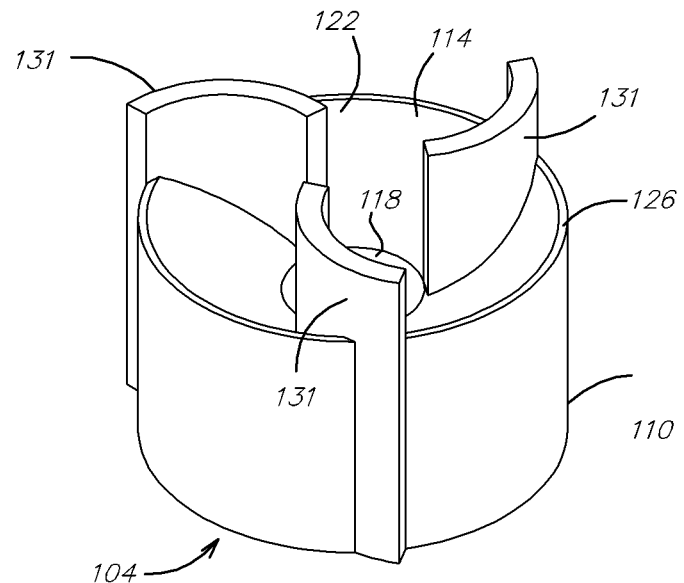
FIGS. 14A and 14B are a perspective view (FIG. 14A) and a top view (FIG. 14B) schematically illustrating an embodiment of an impingement member comprising blades that may assist forming a vortex flow in fluid in a tooth during treatment.
Figure 14B:
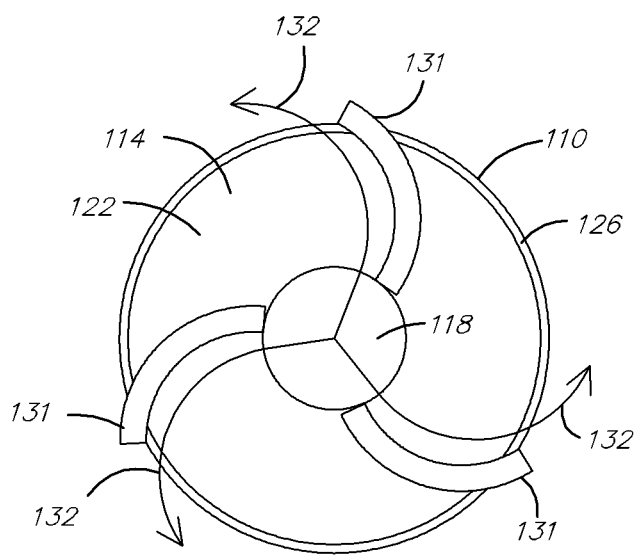

FIGS. 14A and 14B are a perspective view (FIG. 14A) and a top view (FIG. 14B) schematically illustrating an embodiment of an impingement member 110 comprising blades 131 to assist forming a vortex flow or circulation in the fluid in the tooth during treatment. In this embodiment, three curved blades 131 are substantially symmetrically disposed around the impingement member 110. In other embodiments, a different number of blades 131 can be used (e.g., one, two, four, or more), and the blades 130 may be straight or may be shaped or curved differently than shown in FIGS. 14A and 14B. Arrows 132 indicate the direction of the vortex flow or circulation that may be induced, at least in part, by the blades 131, which in this case is counter-clockwise (as seen from the top view in FIG. 14B). In other embodiments, the blades 131 may be configured to produce a clockwise vortex flow or circulation. In other embodiments, additionally or alternatively to the blades 130, the impingement surface 114 may include grooves, ridges, or other features to induce vorticity or circulation, or to otherwise modify the liquid flow or jet spray. In some treatment methods, the distal end 104 of the guide tube 100 can be positioned off-center in the tooth 10 to assist forming fluid circulation or vorticity.

Figure 15A:
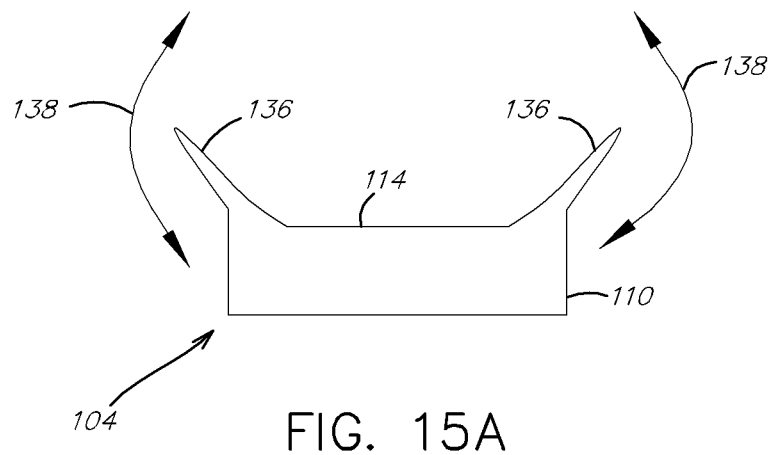
FIGS. 15A-15C are side views of embodiments of impingement members that include flexible portions to assist inducing circulation into the fluid in the tooth during treatment.
Figure 15B:
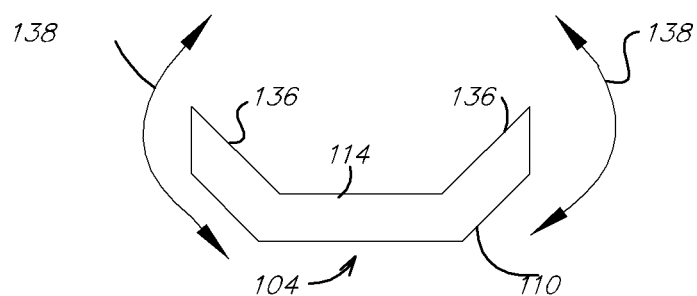
Figure 15C:
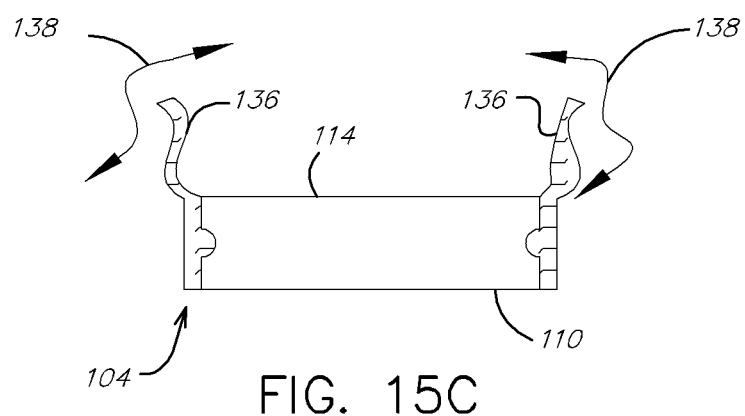

FIGS. 15A-15C are side views of embodiments of impingement members 110 that include flexible portions 136 to assist inducing circulation into the fluid in the tooth 10 during treatment. The flexible portions 136 may be relatively thin so that the portions 136 can flex (as shown by arrows 138) as the jet impinges on the impingement surface 114 and fluid flows across the flexible portions 136. For example, it is believed, although not required, that the jet entrains fluid as it propagates toward the impingement surface 114 and, due to the variable nature of the fluid entrainment, the jet may not impinge at precisely the same location over time (e.g., the impingement point may oscillate across the impingement surface 114). Therefore, the fluid flow past the flexible portions 136 may also be variable, vibratory, or oscillatory, and the flexible portions 136 may adjust their shapes and positions in response to the resulting variable fluid forces. Flexure, vibration, or motion of the flexible portions 136 therefore may aid the impingement member 110 in generating fluid circulation or fluid agitation near the distal end 104 of the guide tube 100. In some embodiments, the flexible portions 136 can be formed by laser machining, wire EDM cutting, or injection molding. In the embodiment shown in FIG. 15C, the flexible portions 136 comprise a flexible material (e.g., an elastomer) that can be attached or bonded to the impingement member 110.

Figure 16A:
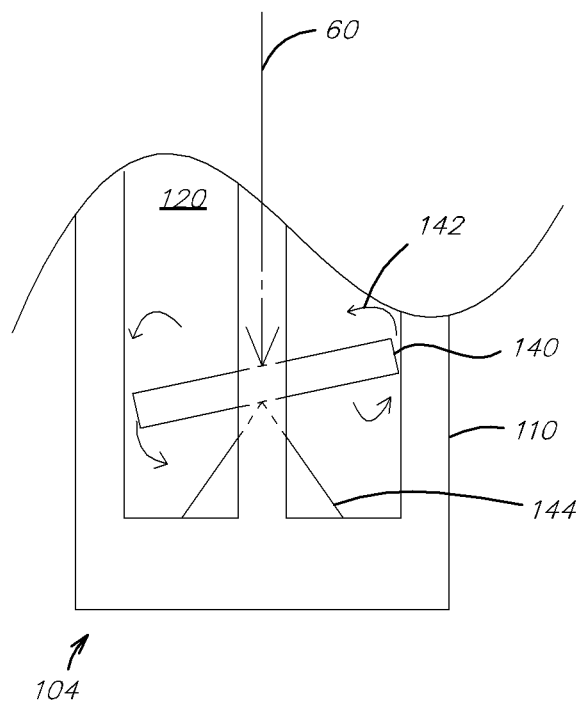
FIGS. 16A and 16B are side views that schematically illustrate further embodiments of the guide tube that may assist in forming a variable fluid circulation near the distal end of the guide tube.
Figure 16B:
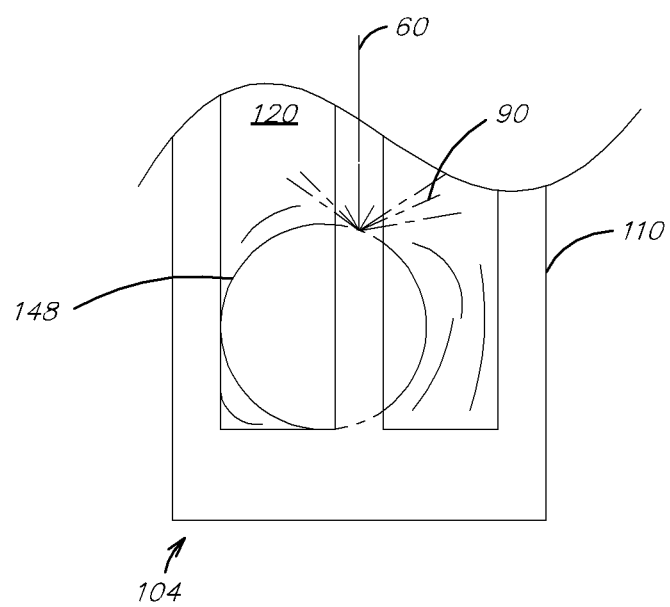

FIGS. 16A and 16B are side views that schematically illustrate further embodiments of the guide tube 100, which may assist in forming a variable fluid circulation near the distal end 104 of the guide tube. As discussed above, variable entrainment of fluid can cause the liquid jet 60 to oscillate slightly as it propagates near the distal end 104 of the guide tube 100. In the embodiment shown in FIG. 16A, a plate 140 mounted on fulcrum 144 (e.g., via a ball-and-socket hinge) can oscillate in directions indicated by arrows 142 as the liquid jet 60 variably impinges on the plate 140. In the embodiment shown in FIG. 16B, a ball 148 having a diameter slightly less than the diameter of the channel 84 is disposed on the impingement member 110. The ball 148 can oscillate and alter the direction and characteristics of the spray 90 produced by impingement of the jet 60 onto the surface of the ball 148.

Figure 17A:
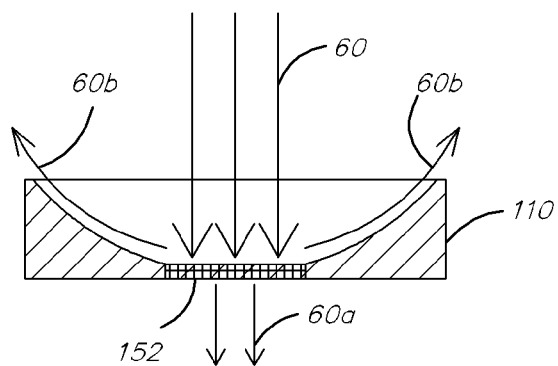
FIGS. 17A-17D schematically illustrate embodiments of an impingement member comprising a material at least partially permeable to the liquid jet.
Figure 17B:
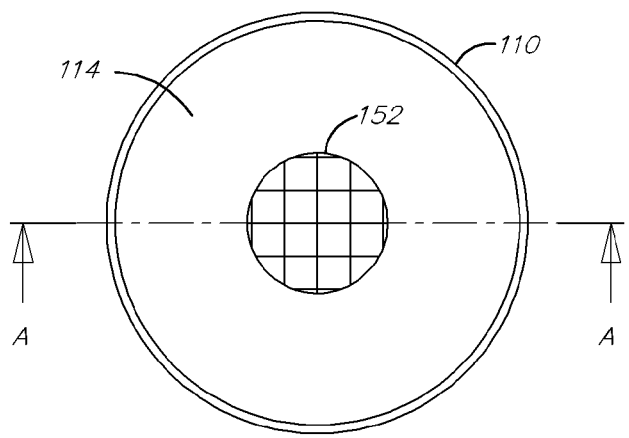
Figure 17C:
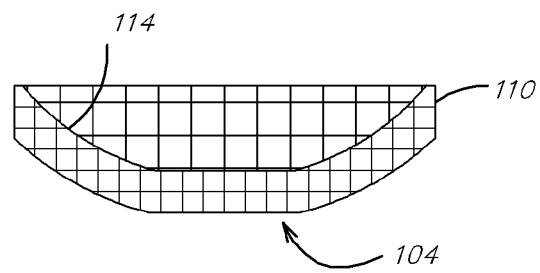

FIGS. 17A-17D schematically illustrate embodiments of an impingement member 110 comprising a permeable material. FIG. 17A is a side view along the line A-A shown in FIG. 17B. FIG. 17C is a side view along the line C-C shown in FIG. 17D. In the embodiment of the impingement member 110 shown in FIGS. 17A and 17B, a region 152 of the impingement member 110 on which the jet 60 impinges comprises the permeable material. The permeable material may be at least partly permeable to the liquid of the jet 60, which may allow some of the jet liquid to pass through the material (schematically illustrated by arrows 60a) and some of the jet liquid to be deflected (schematically illustrated by arrows 60b). It is believed, although not required, that jet liquid 60a that passes through the permeable material may help promote fluid circulation or fluid agitation in the pulp cavity 26 during treatment.

Figure 17D:
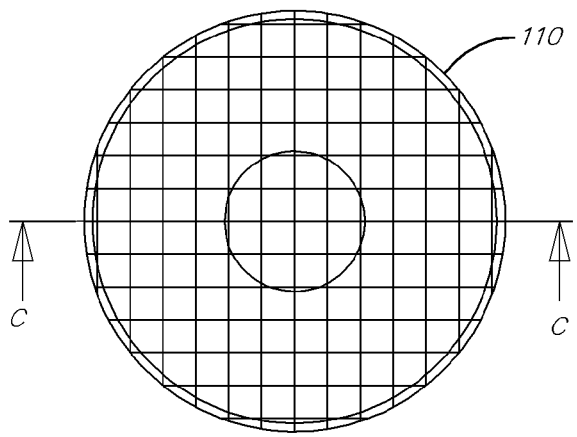

The permeable material may comprise mesh, screen, or a porous material. In some implementations, the permeable material comprises one or more layers of a woven metallic mesh. In some implementations, the permeable material is porous such as, e.g., a machined material comprising openings sized smaller than the cross-sectional size of the jet which act to at least partially inhibit flow of the jet liquid through the porous material. In various embodiments, some or all of the impingement member 110 may be formed from one or more permeable materials. For example, FIGS. 17C and 17D depict an embodiment in which substantially all of the impingement member 110 comprises a woven mesh.

Figure 18:
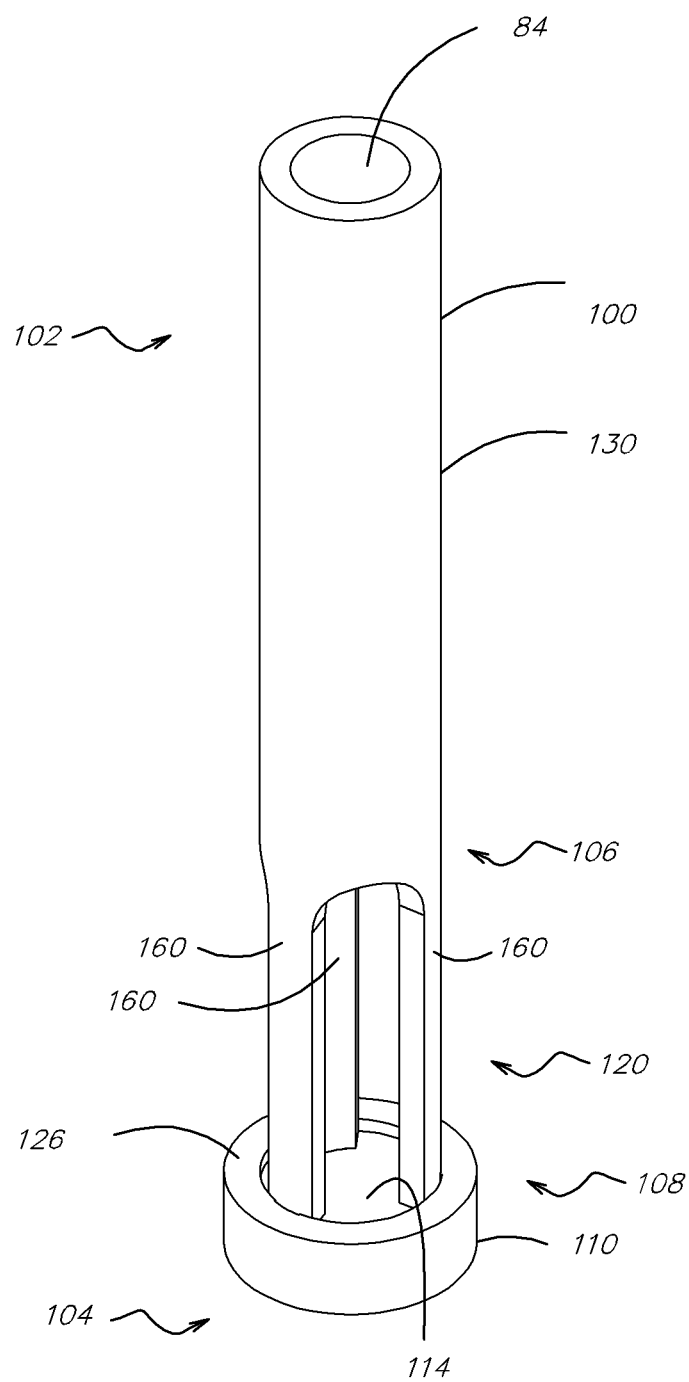
FIG. 18 is a perspective view schematically illustrating an embodiment of a guide tube comprising posts disposed near the distal end of the guide tube.

FIG. 18 is a perspective view schematically illustrating an embodiment of a guide tube 100 comprising posts 160 disposed near the distal end 104 of the guide tube 100. In the embodiment shown in FIG. 18, the guide tube 100 can have three posts 160 associated with three openings 120. In other embodiments, the guide tube 100 may comprise a different number of posts (and/or openings), e.g., one, two, four, five, six, or more (see, e.g., FIGS. 19A-19E and 20A-20E). Portions of the guide tube 100 and/or the posts 160 can be formed by laser cutting, laser welding, metal injection molding, EDM, or other fabrication techniques. For example, in some fabrication techniques, the openings 120 are laser cut from the guide tube 100, thereby forming the posts 160. The posts 160 may extend substantially from the proximal end 106 to the distal end 108 of the openings 120. The impingement member 110 can be formed separately and attached to the body 130 of the guide tube 100 or can be formed integrally with the guide tube 100 (e.g., during metal injection molding of the guide tube).

The size, cross-sectional shape, orientation, and/or angular position of the posts 160 can be different than shown in FIG. 18. For example, each of FIGS. 19A-19E includes a perspective view (upper figure) and a cross-section view (lower figure), taken along the line 19-19 of the upper figure, schematically illustrating an alternate embodiment of a guide tube 100 comprising posts 160. The posts 160 can have cross-sectional shapes that are circular, polygonal, arcuate, wedge-shaped, etc. In any particular embodiment of the guide tube 100, one (or more) of the posts 160 can be sized, shaped, or oriented differently from one (or more) other posts 160. One or more of the posts 160 may be curved and/or angled (see, e.g., FIG. 19C) which may help induce vorticity or fluid circulation in the fluid surrounding the distal end 104 of the guide tube 100.

The size, shape, orientation, and/or angular distribution of the posts 160 (or the size, shape, orientation, and/or angular distribution of the openings 120) can be used to, at least in part, control the angular distribution of the spray 90 produced when the liquid jet 60 impinges on the impingement plate 110. For example, by suitably configuring the posts 160 and/or the openings 120, the angular distribution of the spray (as viewed from the direction of the liquid jet 60) can be made to have a desired angular pattern, be made to be approximately symmetric (e.g., having two-, three-, four-, or higher-order rotational symmetry about the jet axis), be made to be non-symmetric, or be made to have some other angular distribution about the jet axis.

FIGS. 20A-20E are top views that schematically illustrate some possible examples of distributions of the spray 90 that can be produced by various embodiments of guide tubes comprising posts 160 and/or openings 120. In certain implementations, the spray 90 can exit the guide tube 100 through the opening(s) 120, or, alternatively, be thought of as being substantially blocked by the posts 160. A desired angular width of the spray 90 can be selected by suitably selecting the angular size of the post(s) 160 (and/or the opening(s) 120). For example, the angular width of the spray may be about 360 degrees to provide spray to substantially all regions surrounding the distal end 58 of the guide tube 100. In other embodiments, the angular width of a spray may be about 270 degrees, about 180 degrees, about 120 degrees, about 90 degrees, about 60 degrees, about 45 degrees, about 30 degrees, about 20 degrees, or about 10 degrees. Sprays having relatively narrow angular widths (e.g., about 10 degrees to about 30 degrees) may be used to direct energy of the jet or spray toward a desired location in or near a tooth. In various embodiments, the angular width of a spray may be in a range from about 30 degrees to about 60 degrees, about 45 degrees to about 90 degrees, about 100 degrees to about 145 degrees, about 120 degrees to about 240 degrees, or some other range.

Figure 20A:
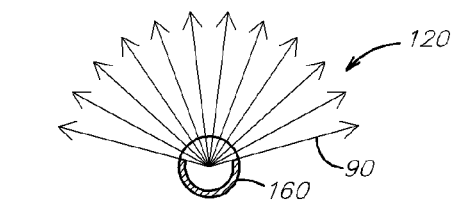
FIGS. 20A-20E are top views schematically illustrating examples of distributions of the spray that can be produced by various embodiments of guide tubes comprising posts and/or openings.
Figure 20B:
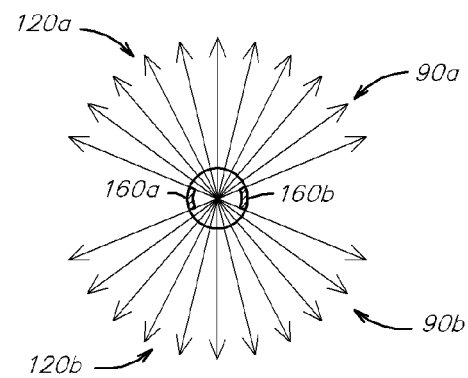
Figure 20C:
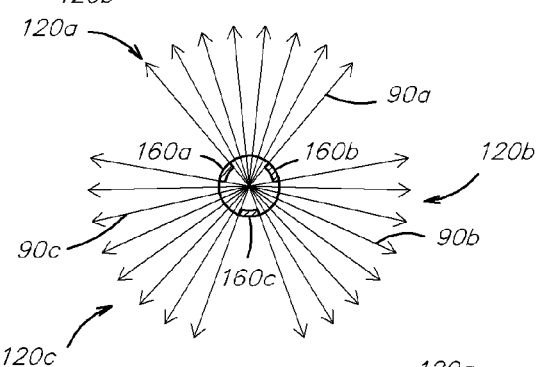
Figure 20D:
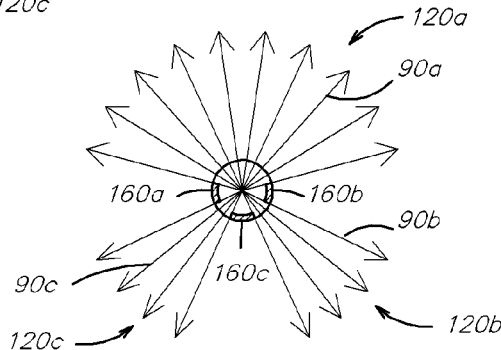
Figure 20E:
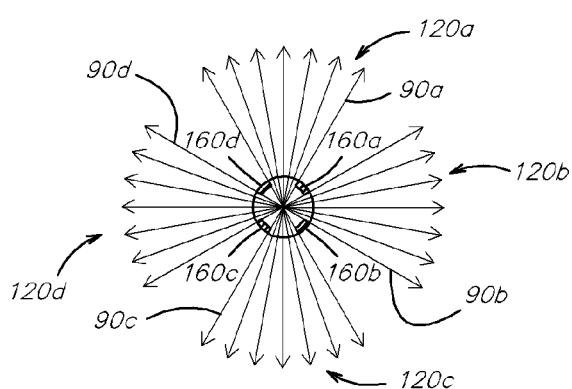

In FIGS. 20A-20E, spray is schematically represented by outwardly-pointing arrows. FIG. 20A schematically illustrates one post 160 and one opening 120, with the spray 90 being directed through the opening 120 substantially toward one side of the guide tube 100 (e.g., toward the top of FIG. 20A). FIG. 20B schematically illustrates two posts 160a, 160b and two openings 120a, 120b that are spaced about 180 degrees apart to provide a spray 90 having two-fold rotational symmetry about the jet (or guide tube or channel) axis. FIGS. 20C and 20D schematically three posts 160a-160c and three openings 120a-120c. In FIG. 20C, the posts 160a-160c and the openings 120a-120c are spaced substantially symmetrically to produce a spray having substantially three-fold rotational symmetry. In FIG. 20D, the posts 160a, 160b are positioned closer to the post 160c (e.g., the angular width of the opening 120a is larger than the angular widths of the openings 120b, 120c) so that more of the liquid is deflected to the spray 90a than the sprays 90b, 90c. In FIG. 20E, four posts 160a-160d and four openings 120a-120d are used to provide a spray 90*a*-90*d* having substantially four-fold rotational symmetry. In other embodiments, the post(s) 160 and/or the opening(s) 120 can be configured differently than shown in FIGS. 20A-20E to produce a spray 90 having desired characteristics.

Figure 21A:
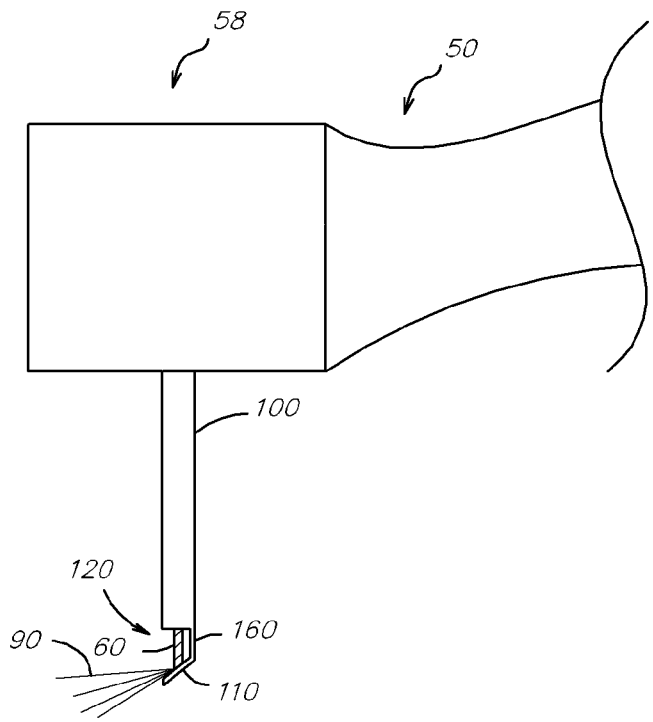
FIGS. 21A-21C are side views schematically illustrating embodiments of guide tubes having curved or angled impingement members.

In many of the guide tube embodiments described herein, the impingement member 110 can be oriented approximately perpendicularly with respect to the longitudinal axis 80 along which the jet 60 propagates (or to the longitudinal axis 86 of the channel 84 or the longitudinal axis of the guide tube 100). In other embodiments, the impingement member 110 can be oriented at an angle that is non-perpendicular with respect to the longitudinal axis 80 along which the jet 60 propagates (or to the longitudinal axis 86 of the channel 84 or the longitudinal axis of the guide tube 100). For example, FIG. 21A is a side view that shows an embodiment of a guide tube 100 having an impingement member 110 that is not oriented perpendicular to the axis 80 of the liquid jet 60 (which in this example propagates along the channel axis 86 and the guide tube axis). Any of the embodiments of impingement members 110 described herein (including, but not limited to, the impingement members shown in FIGS. 12A-17D) can be oriented non-perpendicularly to the jet, channel, or guide tube axis. The orientation of the impingement member 110 may be used to direct or deflect the spray toward desired locations (e.g., away from canal spaces during treatment) or to assist providing a desired fluid circulation or agitation in the tooth during treatment.

Figure 21B:
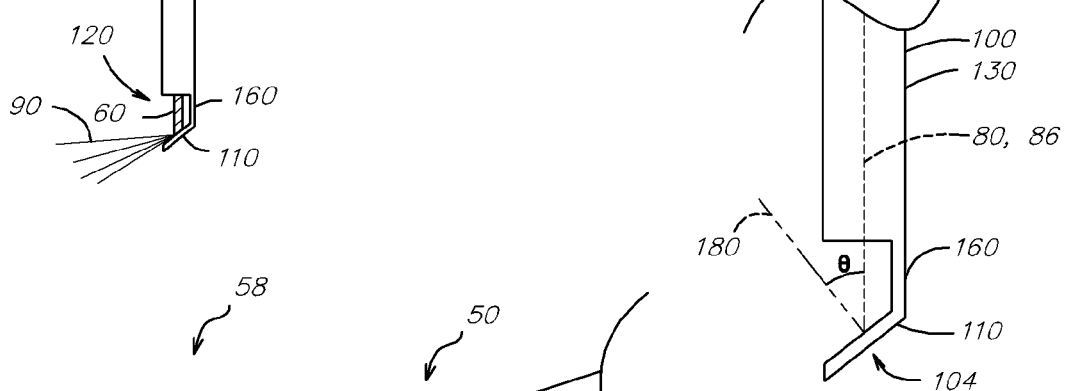

FIG. 21B is a side view that schematically illustrates an angle θ that may be used to describe an orientation of the impingement member 110 with respect to the guide tube 100. In FIG. 21B, the angle θ is defined between the jet axis 80, the channel axis 86, or the guide tube axis (not labeled in FIG. 21B, but collinear with the channel axis 86 in this example) and a normal 180 to the impingement member 110. For guide tubes 100 in which the angle θ is about zero degrees, the impingement member 110 is approximately perpendicular to the jet, channel, or guide tube axis, as appropriate. In the example shown in FIG. 21B, the angle θ is positive when the impingement member 110 is angled away from the proximal end 106 of the opening 120 (e.g., angled downward as shown in FIG. 21B), and the angle θ is negative when the impingement member 110 is angled toward the proximal end 106 of the opening 120 (e.g., upward in FIG. 21B). When the angle θ is positive, the spray 90 will tend to be deflected away from the distal end 104 of the guide tube 100 (see, e.g., the example schematically shown in FIG. 21A). When the angle θ is negative, the spray 90 will tend to be deflected toward the distal end 104 of the guide tube 100. In various embodiments, either positive values or negative values of the angle θ may be utilized to tend to direct the spray 90 away from or toward, respectively, the distal end 104 of the guide tube 100. The absolute magnitude of the angle θ may be about 0 degrees, about 10 degrees, about 20 degrees, about 30 degrees, about 45 degrees, about 50 degrees, about 60 degrees, about 70 degrees, or about 80 degrees. In various embodiments, the absolute magnitude of the angle θ may be in a range from about 0 degrees to about 80 degrees, about 20 degrees to about 60 degrees, about 30 degrees to about 50 degrees, or some other range. In some embodiments, the angle θ can be adjustable by an operator and may be set or changed to a desired angle prior to (or during) dental treatment.

Figure 21C:
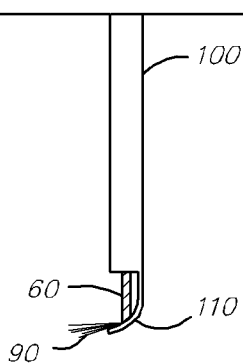

FIG. 21C is a side view that shows an embodiment of a guide tube 100 comprising a curved impingement member 110. In this example, the impingement member 110 is shaped as an arcuate flap that extends away from the proximal end 106 of the opening 120. The curvature of the impingement member 110 may be selected to provide a desired direction or distribution of the spray 90. In some embodiments, two, three, four or more curved impingement members can be used.

Figure 22A:
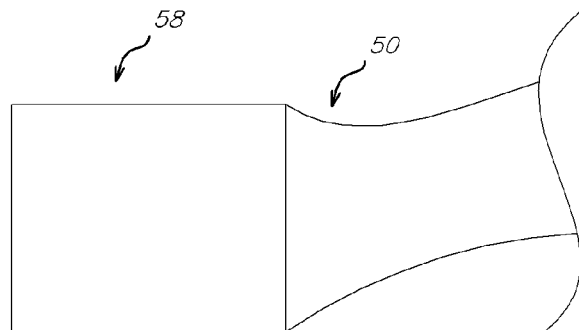
FIGS. 22A-22C are cross-section views schematically illustrating embodiments of handpieces in which nozzle is not oriented perpendicular to the axis of the guide tube.
Figure 22B:
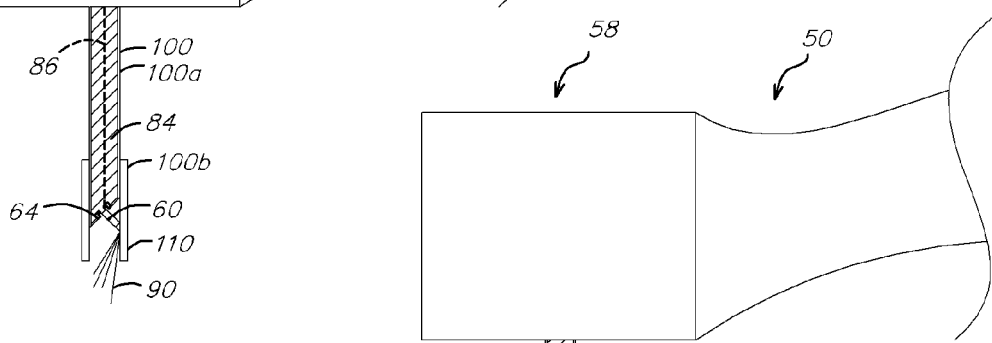
Figure 22C:
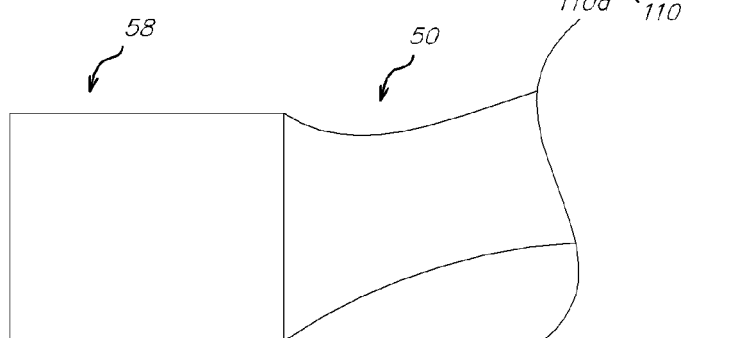

FIGS. 22A-22C are cross-section views schematically illustrating embodiments of handpieces 50 comprising nozzles 64 that are not oriented perpendicular to the axis 86 of the channel 84 in the guide tube 100 or the axis of the guide tube 100. In FIGS. 22A-22C, the nozzle 64 is disposed toward the distal end 58 of the guide tube 100. The nozzle 64 can be angled such that the liquid jet 60 emitted from the orifice 66 of the nozzle 64 propagates along a jet axis 80 that forms an angle with respect to the longitudinal axis 86 of the channel 84. The angle may be about 0 degrees (e.g., the jet 60 is emitted substantially along the channel axis 86), about 10 degrees, about 20 degrees, about 30 degrees, about 45 degrees, about 50 degrees, about 60 degrees, about 70 degrees, about 80 degrees, or about 90 degrees. In various embodiments, the angle may be in a range from about 0 degrees to about 80 degrees, about 20 degrees to about 60 degrees, about 30 degrees to about 50 degrees, about 50 degrees to about 90 degrees, or some other range. In some embodiments, the angle can be adjustable by an operator and may be set or changed to a desired angle prior to (or during) dental treatment. In some embodiments, the guide tube 100 comprises an opening through which the jet 60 from the nozzle 64 exits the guide tube. In some embodiments, the nozzle 64 (or multiple nozzles or orifices) may be formed in or on a side wall of the guide tube 100. In some such embodiments, one (or more) jets, beams, or sprays may be delivered from such nozzles or openings. In some such cases, the jets, beams, or sprays are delivered at angles that are approximately perpendicular to the longitudinal axis of the guide tube 100 or channel 84. In other such cases, one or more nozzles 64 or orifices 66 in the side wall of the guide tube 100 can be oriented toward the distal end 104 of the guide tube 100 (e.g., to direct the jet, beam, or spray toward the distal end 104) and/or can be oriented toward the proximal end 102 of the guide tube 100 (e.g., to direct the jet, beam, or spray toward the proximal end 102).

In the embodiment shown in FIG. 22A, the impingement member 110 comprises an outer tube 100*a* that is disposed around a distal end of an inner tube 100*b*. As the jet 60 exits the angled nozzle 64, the jet 60 impacts an inner surface of the outer tube 100*a* and is deflected into the spray 90. In the embodiments shown in FIGS. 22B and 22C, the impingement member 110 comprises one or more flaps, plates, or structures 110*a*, 110*b* upon which the jet 60 can impinge and be deflected into the spray 90. The size, shape, orientation, and/or arrangement of the flaps, plates, or structures can be selected to provide a desired direction or distribution of the spray 90.

Figure 23:
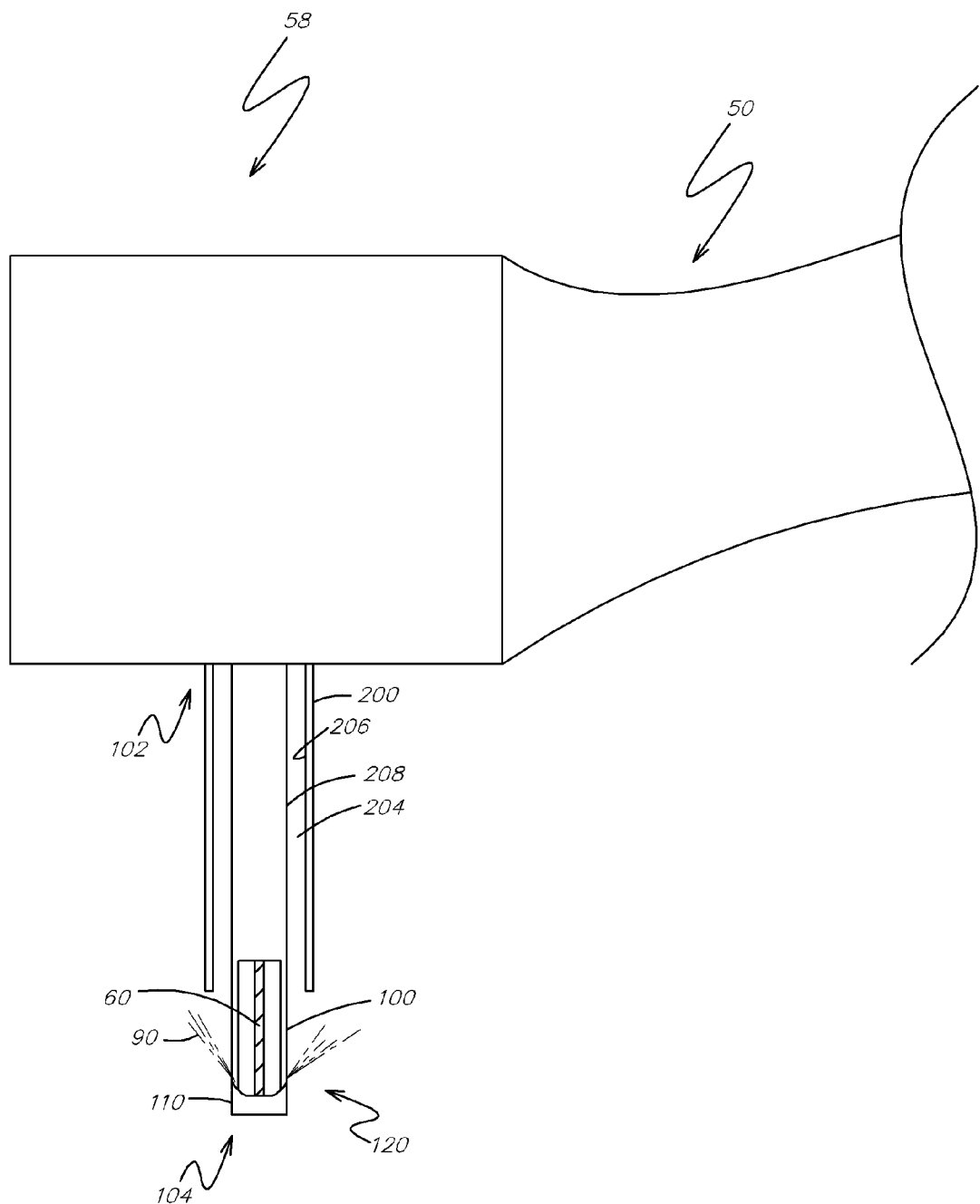
FIG. 23 schematically illustrates an embodiment of a handpiece comprising a liquid flow tube configured to provide a stream of liquid to a tooth location.

FIG. 23 schematically illustrates an embodiment of a handpiece 50 comprising a liquid flow tube 200 configured to provide a stream of liquid to a tooth location. FIG. 23 is a partial cutaway view in which the flow tube 200 is cutaway to show the guide tube 100 disposed in the flow tube. In the illustrated embodiment, the flow tube 200 is disposed around the guide tube 100, and the stream of liquid flows in a channel 204 between an outer surface 208 of the guide tube 100 and an inner surface 206 of the flow tube 200. The stream of liquid may increase the amount of fluid or induce additional circulation in the pulp cavity 26 during treatment. The stream of liquid may also reduce or prevent introduction of air into the pulp cavity 26 during treatment. The liquid provided by the flow tube 200 may, but need not, be different from the liquid used for the jet 60. The handpiece 50 may be configured so that an operator can provide the stream of liquid from the flow tube 200 additionally or alternatively to the jet 60. In some treatments, the flow tube 200 can be used to provide an antiseptic or antibiotic solution (e.g., a bleach such as sodium hypochlorite), a solution with chemicals or medications, or some other liquid. In other embodiments, the flow tube 200 can be disposed adjacent the guide tube 100 or multiple flow tubes 200 can be used. In some embodiments, additionally or alternatively to the flow tube 200, a stream of liquid can be provided along the channel 84 of the guide tube 100.

FIGS. 24A-24F are cross-section views schematically illustrating embodiments of guide tubes 100 having a variety of configurations at the distal end 104 of the guide tube 100. FIGS. 24A and 24B schematically illustrate guide tube embodiments in which the distance between the impingement surface 114 and a distal-most surface 114a of the of the impingement member 110 is different. This distance can act to separate the impingement surface 114 from the floor of the pulp chamber 28 or the canal spaces 30 and may reduce the likelihood that during treatment an operator will position the impingement surface 114 too close to the floor or canal spaces. One or more portions of the distal-most surface 114a (or other surfaces near the distal end 104) may be substantially flat (see, e.g., FIGS. 22A-22B), curved (e.g., partially spherical or elliptical; see, e.g., FIG. 22E), conical or pyramidal (see, e.g., FIGS. 22D, 22F), or textured, roughened, or irregular (see, e.g., FIG. 22C). The distal-most surface 114a may include a tip 116 (see, e.g., FIGS. 22D, 22E), which may be rounded or sharp. Texturing or a tip on the surface 114a may assist the operator in positioning the distal end 104 of the guide tube 100 at or near a desired location in or on a tooth.

In some implementations, the impingement surface 114 (or other surfaces of the guide tube) may be coated with one or more substances that resists degradation of the surface 114 under the influence of, e.g., fluid stresses from impingement of the jet 60, cavitation near the distal end 104 of the guide tube 100, and so forth. In some such implementations, the impingement member 110 can be formed from a material that is relatively easy to shape, machine, mold, or form but which may tend to wear under the impingement stresses or cavitation. The coating may advantageously protect such material. One or more coatings may be applied to the impingement surface 114a (or other surfaces of the guide tube). Methods including, e.g., plating, chemical solution deposition (CSD), chemical vapor deposition (CVD), plasma enhanced CVD, sputtering, pulsed laser deposition, cathodic arc deposition (arc-PVC), or physical vapor deposition (PVD) can be used to form the coating(s).

In some embodiments, the coating can be about 1 to about 7 micron thick, and in some instances (e.g., PVD), may comprise different alloys depending on the amount of wear resistance desired. For example, the alloys may include titanium nitride (TiN), titanium carbon nitride (TiCN), titanium aluminum nitride (TiAlN), aluminum titanium nitride (AlTiN), titanium aluminum silicon nitride (TiAlSiN), zirconium nitride (ZrN), chromium nitride (CrN), or aluminum chromium nitride (AlCrN). Coatings can include materials such as nickel titanium (NiTi) or diamond. In some cases, a coating comprising one or more of these alloys may be able to increase the surface hardness of the impingement surface to be in a range from about 1500 HV to about 3500 HV (HV is the Vickers pyramid number) in hardness on the Vickers scale. In other cases the coating may have a hardness in a range from about 500 HV to about 1000 HV, from about 1000 HV to about 4000 HV, or some other range.

In one implementation, the impingement member 110 and the impingement surface 114 are machined and laser manufactured out of 301 stainless steel in the full hard condition (e.g., with a hardness of about 44 HRC on the Rockwell scale, which is approximately 434 HV on the Vickers scale). The impingement surface 114 is then coated with a 1.5 micron thick layer of AlTiN via PVD. In various embodiments, some or all of the guide tube 100 can be formed from stainless steel (e.g., austentic or 300 series stainless steel, ferritic or martensitic stainless steel), carbon steel, titanium, or nickel. In some embodiments, the guide tube 100 is formed from INCONEL® available from Special Metals Corporation, New Hartford, N.Y., for example, INCONEL 625 or INCONEL 750 X. Further examples of materials that can be used for embodiments of the guide tube 100 include, but are not limited to, Zirconia YTZB, cobalt alloys such as, e.g., CoCrWNi or CoCrMo MP35N, stellite alloys such as, e.g., STELLITE® 33 available from Deloro Stellite, Goshen, Ind., HASTELLOY® alloys available from Haynes International, Inc., Kokomo, Ind., graphene, diamond, silicon nitride, nano-particulated stainless steels, nanocrystalline alloys such as, e.g., NANOVATE®, available from Integran, Pittsburgh, Pa., ceramics, and so forth. In some embodiments, other materials may be used such as, for example, rigid polymeric materials, carbon nanotubes, boron fiber composite tubes, tungsten fiber composite tubes, etc. In some implementations, the material can comprise fibers embedded in rigid polymeric materials and/or metals. Other materials include metal-matrix composites and/or ceramic-metal composites. In some embodiments, different portions of the guide tube 100 are formed from different materials and/or from combinations of any of the above materials.

Figure 25:
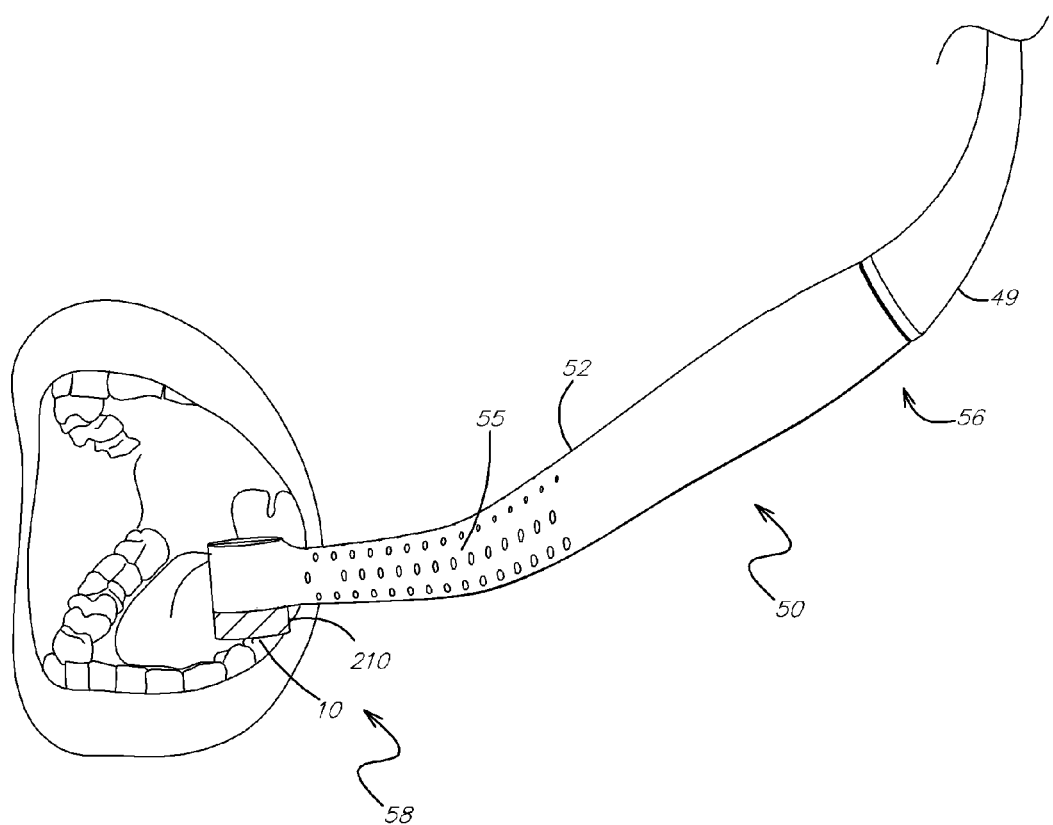
FIG. 25 schematically illustrates use of a handpiece during a dental treatment.

FIG. 25 schematically illustrates use of a handpiece 50 during a dental treatment such as, e.g., a root canal procedure. A drill or grinding tool can initially be used to make an opening (not shown in FIG. 25) in the tooth 10. The opening may extend through the enamel 22 and the dentin 20 to expose and provide access to pulp in the pulp cavity 26. The opening may be made in a top portion of the crown 12 of the tooth 10 or in another portion such as a side of the crown 12 or in the root 16 below the gum 14. The opening may be sized and shaped as needed to provide suitable access to the diseased pulp and/or some or all of the canal spaces 30. The handpiece 50 may be used to deliver a jet 60 of liquid to a portion of the tooth 10 such as, e.g., the pulp cavity 26. The jet 60 advantageously may, but need not, be a CC jet. In some treatment methods, the operator can maneuver the handpiece 50 to direct the jet 60 (or the spray 90) around the pulp chamber 28, if desired during the treatment process.

The handpiece 50 may comprise any of the embodiments of the handpieces 50 described herein. The handpiece 50 may comprise any of the guide tubes 100 or other structures, elements, or features described herein (e.g., the impingement member 100, the opening 120, the flow tube 200, etc.) in any suitable combination. As some non-limiting examples, any of the embodiments of the handpieces 50 shown and described with reference to FIG. 3, 4, 4A, 6, 7A-7B, 9A-9C, 21A-21B, 22A-22C, 23, or 25 can be used with any of the embodiments of the guide tubes 100 shown and described with reference to the foregoing figures and/or to FIGS. 8A-8C, 10A-10F, 11A-11D, 16A-16B, 18, 19A-19E, and/or 24A-24F. Also, any of the embodiments of the guide tubes 100 described with reference to the foregoing figures may utilize the impingement members 110 shown and described with reference to the foregoing figures and/or to FIGS. 12A-12E, 13A-13E, 14A-14B, 15A-15C, 17A-17D, and/or 20A-20E.

The handpiece 50 can be positioned by an operator so that the distal end 104 of the guide tube 100 is disposed at a desired location in, on, or near the tooth 10 or a tooth surface (e.g., a dentinal surface). For example, the distal end 104 of the guide tube 100 may be disposed in the pulp cavity 26 of the tooth. The handpiece 50 can be used to provide a high-velocity liquid beam (e.g., a CC jet in some treatments) that may generate a pressure wave that can propagate through the tooth 10 or root canal system 30 and can detach organic material from the tooth 10 or dentinal surfaces. The liquid beam and/or the pressure wave may cause or increase the efficacy of various effects that may occur in the tooth including, but not limited to, acoustic cavitation (e.g., bubble formation and collapse, microjet formation), fluid agitation, fluid circulation, sonoporation, sonochemistry, and so forth. In some treatment methods, submersing the distal end 104 of the guide tube 100 in fluid in the tooth 10 under treatment may increase the efficacy of some or all of the foregoing effects, which may lead to effective cleaning of the root canal spaces 30. In certain treatment methods, the nozzle 64 may be disposed toward the distal end 104 of the guide tube 100 so that the orifice 66 of the nozzle 64 is submersed in fluid in the tooth under treatment. In certain such embodiments, the liquid jet emerging from the orifice 66 is delivered in a fluid, rather than air, environment and may, in some cases, provide an acoustic field that may be larger than an acoustic field obtainable from a liquid jet formed in an air environment that subsequently impacts fluid in the tooth.

Optionally, a flow restrictor 210 can be disposed at the distal end 58 of the handpiece 50. In some treatment methods, the flow restrictor 210 can be used to inhibit backflow of fluid from the tooth under treatment. For example, the flow restrictor 210 may inhibit backflow of fluid out of an opening in the tooth 10. The flow restrictor 210 can be substantially cylindrical and can substantially surround the guide tube 100. The flow restrictor 210 may be configured to contact a portion of the tooth 10 during the dental treatment. In some cases, the flow restrictor 210 is disposed loosely around the guide tube 100. The flow restrictor 210 may be removably attached to the guide tube 100 in some cases. The flow restrictor 210 can be configured to conform to the crown of the tooth 30 under treatment. The flow restrictor 210 may help to contain fluid or reduce or inhibit backflow of liquid that emanates from the distal end 104 of the guide tube 100 (e.g., jet or spray from the opening 120), liquid that is delivered into the tooth from a flow tube 200 (if used), fluid within the pulp cavity, and so forth. The flow restrictor 210 can be configured such that jet or spray that emerges from the opening 120 (or liquid from other sources such as, e.g., the flow tube 200) is sufficiently retained within the pulp cavity 26 so that the distal end 104 of the guide tube 100 may be contained or submersed in the fluid. The opening 120 of the guide tube 100 can be contained or submersed in fluid in the tooth 10. For example, both the proximal end 106 and the distal end 108 of the opening 120 can be contained in fluid in the tooth, e.g., for a lower tooth 10, both the proximal end 106 and the distal end 108 of the opening 120 can be submersed below the level of fluid in the tooth. In some treatment methods, the guide tube 100 may be disposed in a tooth cavity such that only a portion of the opening 120 is contained within fluid (e.g., one of the proximal end 106 or the distal end 108 is contained in fluid). It is believed (although not required) that treatment methods utilizing a flow restrictor 219 may improve the opportunities for cavitation and pressures waves to be formed in the tooth 30. The flow restrictor 210 can be configured such that the liquid emerging from the opening 120 of the guide tube 100 is not substantially impeded by the flow restrictor 210. For example, the distal surface of the flow restrictor 210 may not extend to or beyond the proximal end 106 of the opening 120. In some treatment methods, the flow restrictor 210 is applied to the tooth 10, and the handpiece 50 is then maneuvered into position near the tooth 10.

In certain treatment methods, the flow restrictor 210 may, but does not need to, substantially seal the opening to a cavity in the tooth 10 such that the cavity is substantially water tight. For example, in certain treatment methods, the flow restrictor 210 inhibits back flow of fluid out of the cavity but need not prevent all fluid outflow from the tooth 10. For example, in some treatment methods, one or more openings may be formed in the tooth (e.g., via drilling) to allow some fluid to flow out of the cavity in the tooth 10, and the restrictor 210 can be used to reduce or prevent fluid backflow out of other opening(s) (e.g., a coronal access opening).

In some embodiments, the flow restrictor 210 is formed from a material that is not adversely affected by chemicals or irrigation solutions such as, e.g., sodium hypochlorite, used during root canal procedures. The flow restrictor 210 may comprise any suitable porous and/or absorbent material (or materials) such as, e.g., a sponge. For example, the flow restrictor 210 may comprise a porous material (e.g., elastomeric, plastic, rubber, cellulose, fabric, foam, etc.) that can at least partially absorb liquid. The flow restrictor material may be deformable and may be capable of deforming to contours of tooth surfaces. In some embodiments, the flow restrictor 210 comprises a material having a density in a range from about 1 to about 1000 $kg/m^3$, or in a range of about 10 to about 100 $kg/m^3$. The flow restrictor 210 can have a tensile strength in a range from about 1 kPa to about 3000 kPa or in a range of about 50 kPa to about 400 kPa. The flow restrictor 210 can have an ultimate elongation in a range of about 5% to about 800% or in a range of about 50% to about 220%. In some embodiments, the flow restrictor 210 comprises cells and can have a visual cell count in a range of about 1 to about 250/cm or in a range from about 10 to about 40/cm. Material used for the foam may comprise an ester or another type of foam.

Although the tooth 10 schematically depicted in some of the figures is a molar, the procedures may be performed on any type of tooth such as an incisor, a canine, a bicuspid, or a molar. Also, the disclosed apparatus and methods are capable of treating root canal spaces having a wide range of morphologies, including highly curved root canal spaces. Moreover, the disclosed apparatus and methods may be applied to human teeth (including juvenile teeth) and/or on animal teeth.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner, as would be apparent to one of ordinary skill in the art from this disclosure, in one or more embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. A dental instrument comprising:
   a nozzle configured to produce a high-velocity liquid jet;
   a positioning member having a channel through which the high-velocity liquid jet travels, the positioning member having a proximal end portion and a distal end portion;
   an impingement member disposed at the distal end portion of the positioning member and having an impingement surface; and
   a plurality of openings through the distal end portion of the positioning member,
   wherein the impingement member comprises one or more angled or curved portions that angle or curve back towards the proximal end portion of the positioning member, wherein the one or more angled or curved portions extend distally beyond distal ends of the openings, wherein the nozzle is arranged such that the high-velocity liquid jet impacts the impingement surface at a point distally beyond the distal ends of the openings, and wherein the openings are configured to allow outflow of liquid from the liquid jet after impact with the impingement surface.

2. The dental instrument of claim 1, wherein the positioning member comprises an elongated member having a longitudinal axis.

3. The dental instrument of claim 2, wherein at least a portion of the elongated member has a cross-section perpendicular to the longitudinal axis that is substantially circular or substantially polygonal.

4. The dental instrument of claim 2, wherein the elongated member is substantially straight between the proximal end portion and the distal end portion.

5. The dental instrument of claim 2, wherein the channel has a channel axis, and the channel axis is substantially parallel to the longitudinal axis of the elongated member.

6. The dental instrument of claim 5, wherein the elongated member is disposed such that the high-velocity liquid jet propagates along a jet axis that is substantially parallel to the channel axis or the longitudinal axis of the elongated member.

7. The dental instrument of claim 1, wherein the nozzle comprises a proximal surface and a distal surface, the nozzle further comprising an orifice extending from the proximal surface to the distal surface and comprising at least one side wall, the orifice having a width, wherein at least one of the proximal surface, the distal surface, or the side wall has a surface roughness less than about 0.01 times the width of the orifice.

8. The dental instrument of claim 7, wherein the nozzle has a corner forming at least part of the orifice and being disposed between the side wall and the proximal surface, and a ratio of a curvature of the corner to the width of the orifice is less than about 0.1.

9. The dental instrument of claim 7, wherein the orifice has a length between the proximal surface and the distal surface, and the ratio of the length to the width of the orifice is less than about 4.

10. The dental instrument of claim 1, wherein the nozzle is disposed in the proximal end portion of the positioning member.

11. The dental instrument of claim 1, wherein the channel has a channel axis, and the nozzle is disposed in the positioning member so as to at least generally align with the channel axis.

12. The dental instrument of claim 1, wherein the channel has a channel axis, and the nozzle is configured to output the high-velocity liquid jet at an angle to the channel axis.

13. The dental instrument of claim 1, further comprising a backflow restrictor configured to be applied to the tooth and to inhibit backflow of fluid out of an opening in the tooth during operation of the liquid jet, at least a portion of the backflow restrictor disposed between the proximal end portion and the distal end portion of the positioning member.

14. The dental instrument of claim 13, wherein the backflow restrictor is disposed substantially around the positioning member.

15. The dental instrument of claim 13, wherein at least a portion of the backflow restrictor is disposed at or along the proximal end portion of the positioning member.

16. The dental instrument of claim 13, wherein the backflow restrictor comprises a material that is at least partially porous or at least partially absorbent.

17. The dental instrument of claim 13, wherein the backflow restrictor comprises a material that is capable of deforming to contours of the tooth.

18. The dental instrument of claim 13, wherein the backflow restrictor is configured to be coupled to a handpiece.

19. The dental instrument of claim 1, wherein the impingement member is oriented at a non-zero angle to a channel axis of the channel or a longitudinal axis of the positioning member.

20. The dental instrument of claim 1, wherein the impingement surface comprises a concave surface.

21. The dental instrument of claim 1, wherein the impingement surface comprises a convex surface.

22. The dental instrument of claim 1, wherein the one or more angled or curved portions of the impingement member are configured to at least partially direct at least a portion of the liquid jet generally toward the proximal end portion of the positioning member.

23. The dental instrument of claim 1, wherein the one or more angled or curved portions of the impingement member are configured to impart vorticity or circulation to at least a portion of the liquid jet that impacts the impingement surface.

24. The dental instrument of claim 1, wherein the impingement member is configured to produce a spray of liquid upon impact of the liquid jet.

25. The dental instrument of claim 24, wherein the spray of liquid comprises a first spray directed in a first direction and a second spray directed in a second direction, the second direction being substantially different from the first direction.

26. The dental instrument of claim 1, wherein the distal end portion of the positioning member comprises a pointed, rounded, or textured region.

27. The dental instrument of claim 1, further comprising a flow tube configured to deliver a low-velocity stream of fluid to the cavity in a tooth.

28. The dental instrument of claim 27, wherein the positioning member is at least partially disposed in the flow tube.

29. The dental instrument of claim 1, further comprising a handpiece, the positioning member coupled to a distal portion of the handpiece.

30. The dental instrument of claim 1, wherein the distal end portion is configured to be at least partially positioned within a cavity in a tooth so as to direct the liquid jet into the cavity in the tooth.

31. The dental instrument of claim 1, wherein the instrument is configured such that the high-velocity liquid jet propagates along a jet axis and impacts the impingement surface at a portion of the impingement surface that is substantially perpendicular to the jet axis.

32. The dental instrument of claim 1, wherein the positioning member is sized and shaped to be positioned in a portion of a root canal.

33. The dental instrument of claim 1, wherein the nozzle comprises an orifice having a diameter at an outlet or an inlet of the orifice in a range from about 10 microns to about 100 microns, and wherein the positioning member has a width in a range from about 0.1 mm to about 5 mm.

34. The dental instrument of claim 1, wherein each opening of the plurality of openings has a length in a range of 1 mm to 10 mm.

35. A dental instrument comprising:
a positioning member having a channel configured to deliver a high-velocity liquid jet to a tooth, the positioning member having a proximal end portion and a distal end portion; and
an impingement member disposed at the distal end portion of the positioning member and having an impingement surface, the instrument configured such that the high-velocity liquid jet impacts the impingement surface during operation of the high-velocity liquid jet,
wherein the impingement member comprises one or more flexible members.

36. The dental instrument of claim 35, wherein the distal end portion of the positioning member comprises one or more openings configured to allow outflow of liquid from the liquid jet after impact with the impingement surface.

37. A dental instrument comprising:
a positioning member having a channel configured to deliver a high-velocity liquid jet to a tooth, the positioning member having a proximal end portion and a distal end portion; and
an impingement member disposed at the distal end portion of the positioning member and having an impingement surface, the instrument configured such that the high-velocity liquid jet impacts the impingement surface during operation of the high-velocity liquid jet,
wherein at least a portion of the impingement member comprises a material that is at least partially permeable to the liquid jet.

38. The dental instrument of claim 37, wherein the material that is at least partially permeable to the liquid jet comprises mesh.

39. A dental instrument comprising:
a nozzle configured to produce a high-velocity liquid jet;
a guide tube having a proximal portion and a distal portion, the guide tube comprising a channel configured to guide the liquid jet along a jet axis toward the distal portion of the guide tube; and
an impingement member disposed near the distal portion of the guide tube and having an impingement surface, the instrument configured such that the liquid jet impacts the impingement surface during operation of the liquid jet at a portion of the impingement surface that is substantially perpendicular to the jet axis,
wherein the impingement member comprises one or more angled or curved portions that angle or curve back towards the proximal portion of the guide tube, the one or more angled or curved portions being disposed substantially symmetrically relative to the jet axis.

40. The dental instrument of claim 39, wherein the impingement surface comprises a concave surface facing towards the liquid jet.

41. The dental instrument of claim 40, wherein the instrument is configured such that the liquid jet impacts the concave surface at a location where a tangent to the concave surface is substantially perpendicular to the jet axis.

42. The dental instrument of claim 39, wherein the instrument is configured such that the liquid jet impacts the impingement member at a distal-most portion of the impingement surface.

43. The dental instrument of claim 39, wherein the impingement surface comprises a substantially flat surface.

44. The dental instrument of claim 39, further comprising a handpiece, the guide tube coupled to a distal portion of the handpiece.

45. The dental instrument of claim 39, further comprising a backflow restrictor configured to be applied to a tooth and to inhibit backflow of fluid out of an opening in the tooth during operation of the liquid jet, at least a portion of the backflow restrictor disposed between the proximal portion and the distal portion of the guide tube.

46. The dental instrument of claim 39, further comprising a filler material configured to fill a root canal of the tooth.

47. The dental instrument of claim 39, wherein at least a portion of the guide tube has a cross-section perpendicular to the jet axis that is substantially circular or substantially polygonal.

48. The dental instrument of claim 39, wherein the nozzle comprises a proximal surface and a distal surface, the nozzle further comprising an orifice extending from the proximal surface to the distal surface and comprising at least one side wall, the orifice having a width, wherein at least one of the proximal surface, the distal surface, or the side wall has a surface roughness less than about 0.01 times the width of the orifice.

49. The dental instrument of claim 48, wherein the nozzle has a corner forming at least part of the orifice and being disposed between the side wall and the proximal surface, and a ratio of a curvature of the corner to the width of the orifice is less than about 0.1.

50. The dental instrument of claim 48, wherein the orifice has a length between the proximal surface and the distal surface, and the ratio of the length to the width of the orifice is less than about 4.

51. The dental instrument of claim 39, wherein the nozzle is disposed in the proximal portion of the guide tube.

52. The dental instrument of claim 39, wherein the channel has a channel axis, and the nozzle is disposed in the guide tube so as to at least generally align with the channel axis.

53. The dental instrument of claim 39, wherein the one or more angled or curved portions of the impingement member are configured to at least partially direct at least a portion of the liquid jet generally toward the proximal portion of the guide tube.

54. The dental instrument of claim 39, wherein the impingement member is configured to produce a spray of liquid upon impact of the liquid jet.

55. The dental instrument of claim 54, wherein the spray of liquid comprises a first spray directed in a first direction and a second spray directed in a second direction, the second direction being substantially different from the first direction.

56. The dental instrument of claim 39, wherein the distal portion is configured to be at least partially positioned within a cavity in a tooth so as to direct the liquid jet into the cavity in the tooth.

57. The dental instrument of claim 39, further comprising a plurality of openings through the distal portion of the guide tube, the openings configured to allow outflow of liquid from the liquid jet after impact with the impingement surface.

58. The dental instrument of claim 57, wherein the openings are disposed approximately symmetric relative to the jet axis.

59. The dental instrument of claim 39, wherein the nozzle comprises an orifice having a diameter at an outlet or an inlet of the orifice in a range from about 10 microns to about 100 microns, and wherein the guide tube has a width in a range from about 0.1 mm to about 5 mm.

60. A dental instrument comprising:
a nozzle configured to produce a high-velocity liquid jet;
a guide tube having a proximal portion and a distal portion, the guide tube comprising a channel configured to guide the liquid jet toward the distal portion of the guide tube, the channel extending along a longitudinal axis; and
an impingement member disposed near the distal portion of the guide tube and having an impingement surface, the instrument configured such that the liquid jet impacts the impingement surface during operation of the liquid jet,
wherein the impingement surface comprises a concave surface facing the liquid jet, the concave surface substantially symmetric about the longitudinal axis of the channel.

61. The dental instrument of claim 60, wherein the instrument is configured such that the liquid jet impacts the impingement member at a distal-most portion of the impingement surface.

62. The dental instrument of claim 60, further comprising a handpiece, the guide tube coupled to a distal portion of the handpiece.

63. The dental instrument of claim 60, further comprising a filler material configured to fill a root canal of the tooth.

64. The dental instrument of claim 60, wherein at least a portion of the guide tube has a cross-section perpendicular to the longitudinal axis that is substantially circular or substantially polygonal.

65. The dental instrument of claim 60, wherein the nozzle comprises a proximal surface and a distal surface, the nozzle further comprising an orifice extending from the proximal surface to the distal surface and comprising at least one side wall, the orifice having a width, wherein at least one of the proximal surface, the distal surface, or the side wall has a surface roughness less than about 0.01 times the width of the orifice.

66. The dental instrument of claim 65, wherein the nozzle has a corner forming at least part of the orifice and being disposed between the side wall and the proximal surface, and a ratio of a curvature of the corner to the width of the orifice is less than about 0.1.

67. The dental instrument of claim 65, wherein the orifice has a length between the proximal surface and the distal surface, and the ratio of the length to the width of the orifice is less than about 4.

68. The dental instrument of claim 60, wherein the nozzle is disposed in the proximal portion of the guide tube.

69. The dental instrument of claim 60, wherein the nozzle is disposed in the guide tube so as to at least generally align with the longitudinal axis.

70. The dental instrument of claim 60, further comprising a backflow restrictor configured to be applied to a tooth and to inhibit backflow of fluid out of an opening in the tooth during operation of the liquid jet, at least a portion of the backflow restrictor disposed between the proximal portion and the distal portion of the guide tube.

71. The dental instrument of claim 60, wherein the impingement member is configured to at least partially direct at least a portion of the liquid jet generally toward the proximal portion of the guide tube.

72. The dental instrument of claim 60, wherein the impingement member is configured to produce a spray of liquid upon impact of the liquid jet.

73. The dental instrument of claim 72, wherein the spray of liquid comprises a first spray directed in a first direction and a second spray directed in a second direction, the second direction being substantially different from the first direction.

74. The dental instrument of claim 60, wherein the distal portion is configured to be at least partially positioned within a cavity in a tooth so as to direct the liquid jet into the cavity in the tooth.

75. The dental instrument of claim 60, wherein the instrument is configured such that the liquid jet propagates along a jet axis and impacts the impingement surface at a portion of the impingement surface that is substantially perpendicular to the jet axis.

76. The dental instrument of claim 60, wherein the instrument is configured such that the liquid jet propagates along a jet axis and the liquid jet impacts the concave surface at a location where a tangent to the concave surface is substantially perpendicular to the jet axis.

77. The dental instrument of claim 60, further comprising a plurality of openings through the distal portion of the guide tube, the openings configured to allow outflow of liquid from the liquid jet after impact with the impingement surface.

78. The dental instrument of claim 77, wherein the openings are disposed approximately symmetric relative to the longitudinal axis.

79. The dental instrument of claim 60, wherein the nozzle comprises an orifice having a diameter at an outlet or an inlet of the orifice in a range from about 10 microns to about 100 microns, and wherein the guide tube has a width in a range from about 0.1 mm to about 5 mm.

* * * * *